(12) United States Patent
Shi et al.

(10) Patent No.: US 12,297,512 B2
(45) Date of Patent: May 13, 2025

(54) DNA BARCODE FOR VARIETY IDENTIFICATION OF WOLFBERRY AND IDENTIFICATION METHOD THEREFOR

(71) Applicant: Wolfberry Engineering Research Institute, Ningxia Academy of Agriculture and Forestry Sciences, Yinchuan (CN)

(72) Inventors: Zhigang Shi, Ningxia (CN); Ru Wan, Ningxia (CN); Xiuying Wang, Ningxia (CN); Xiyan Zhang, Ningxia (CN); Yunxiang Li, Ningxia (CN); Libin Yang, Ningxia (CN); Xiao Wang, Ningxia (CN); Tinghui Ma, Ningxia (CN)

( * ) Notice: Subject to any disclaimer, the term of this patent is extended or adjusted under 35 U.S.C. 154(b) by 707 days.

(21) Appl. No.: 17/137,191

(22) Filed: Dec. 29, 2020

(65) Prior Publication Data

US 2021/0198756 A1 Jul. 1, 2021

(30) Foreign Application Priority Data

Apr. 28, 2020 (CN) .......................... 202010347886.2
Jun. 30, 2020 (CN) .......................... 202010608982.8

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/13* (2013.01)

(58) Field of Classification Search
None
See application file for complete search history.

(56) References Cited

FOREIGN PATENT DOCUMENTS

CN 110229927 A 9/2019

OTHER PUBLICATIONS

Guan et al. Acta Societatis Botanicorum Poloniae / 2023 / vol. 92 / Article 170979.*
Chinese Traditional and Herbal Drugs, 2016, vol. 47, No. 13, pp. 2328-2332; English translations attached.*
GenBank KT906344.1, Mar. 23, 2016.*
Mehraj et al. (Annals of Agricultural Sciences, vol. 62, Issue 2, Dec. 2017, pp. 211-220).*
WAN RU,Identification of 21 Wolfberry Plants Based on psbA-trnH sequence barcode, Jiangsu Agricultural Sciences, Jan. 31, 2019, China.
Shi Zhigang, Early Screening of Intra-species Hybrids of Lycium barbarum Based on ITS barcode sequence, Jiangsu Agricultural Science, Jun. 30, 2017,China.
Yin Yue, SSR Information Analysis and Molecular Marker Development of the Transcription Group of Lycium barbarum, Journal of Zhejiang A&F University ,Apr. 20, 2019,China.
Shi Zhigang, Genetic Polymorphism of Eighteen Lycium barbarum Resources Based on nrDNA Its Sequence, Agricultural Science & Technology,Sep. 30, 2008,China.
Wan Ru, Identifying Lycium L. Plants Based on matK Sequence as Barcodes,Ningxia Agricultural and Forestry Science and Technology,Sep. 30, 2018,China.

* cited by examiner

*Primary Examiner* — Juliet C Switzer
(74) *Attorney, Agent, or Firm* — Bayramoglu Law Offices LLC

(57) ABSTRACT

The invention belongs to the technical field of species identification of *Lycium chinensis*, specially relating to a DNA barcode for identifying *Lycium chinensis* species and an identification method therefor. The DNA barcorde provide by the present invention can be applied to building a phylogenetic tree to be used for studying intra-species and inter-species phylogeny of *Lycium chinensis*, providing an effective basis for identification, classification and phylogenetic study of *Lycium chinensis*. The invention also provides a trnG-trnS barcode database, to effectively identify the species of the *Lycium chinensis* and determine the interspecies relationship of *Lycium chinensis*, thereby providing an effective basis for the species of *Lycium chinensis*.

3 Claims, 3 Drawing Sheets

Specification includes a Sequence Listing.

(a)

(b)

SEQUENCE LISTING

<160> NUMBER OF SEQ ID NOS: 38

<210> SEQ ID NO 1
<211> LENGTH: 1645
<212> TYPE: DNA
<213> ORGANISM: Ningqi No.1 (L. barbarum Linn)

<400> SEQUENCE: 1

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga aagaatcttt ctttctctct     240
tttcttcttt actatattat atagatatgt acaactttta tcatcaattt cctttatctc     300
tttatctaaa gtaaaggaag ggctcagaag agccaagaat atcaagaaaa ataaagaaga     360
```

```
ccgcttttct tgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc attttaattg aatagttaat attcaagcaa caagaaaaaa    540
ttcccatttt tgctaaaagt aaaaaaaata tatatgaa atagaaaatt cgatcaaaat    600
aaaagtctca tttctctttc tgctttttta tgtttaccat cttgctggac taaaaaaaag    660
aagctttcga gtattccaca atgcatttt atgttatgat tttagtggtt ttgacgaccc    720
tatcttatcc tatcttgatt accacaattc ccctgttcga caaagttgc atttgtatac    780 aataatcgaa ttgtagcggg tatagtttag tggtaaagt gtgattcgtt ctattatccc    840
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aaggtcactt agacattgaa aaattggatt attaaattgc gaaacataat   1020
ttttgaattg gatcaatact tccaattgaa taagtatgaa taaaggatcc atggatgaag   1080
atagaaagtt gatttctaat cgtaactaaa tcttcaattt cttatttgta aagaagaaag   1140
tgaagcaaaa tagctattaa acgatgactt tggtttacta gagacatcaa catattgttt   1200
tagctcggtg gaaacaaaat cctttcctc aggatcctat taaatagaaa tagagaacga   1260
aataactaga aaggttgtta gaatccccct cttctagaag gatcatctac aaagctattc   1320
gttttatctg tattcagatc aaaagctgac atagatgtta tgggtagaat tcttttttt    1380 tttctaattt tgttcacatc ttagatctat aaattgactc atctccataa aggagccgaa   1440
tgaaaccaaa gtttcatgtt cggttttgaa ttagagacgt tcaaataat gaatcgacgt   1500 cgactataac ccctagcctt ccaagctaac gatgcgggtt cgattcccgc tacccgctct   1560 ctatctatt attctaaata ttttaatctt ttcattaaat caaatttagt ttattagtat   1620
tagtacatca ttgaatatac aattc                                        1645

<210> SEQ ID NO 2
<211> LENGTH: 1645
<212> TYPE: DNA
<213> ORGANISM: Ningqi No.2 (L. barbarum Linn)

<400> SEQUENCE: 2
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt actatattat atagatatgt acaactttta tcatcaattt cctttatctc    300
tttatctaaa gtaaaggaag ggctcagaag agccaagaat atcaagaaaa ataagaaga    360 ccgcttttct tgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc attttaattg aatagttaat attcaagcaa caagaaaaaa    540
ttcccatttt tgctaaaagt aaaaaaaata tatatgaa atagaaaatt cgatcaaaat    600
aaaagtctca tttctctttc tgctttttta tgtttaccat cttgctggac taaaaaaaag    660
aagctttcga gtattccaca atgcatttt atgttatgat tttagtggtt ttgacgaccc    720
tatcttatcc tatcttgatt accacaattc ccctgttcga caaagttgc atttgtatac    780 aataatcgaa ttgtagcggg tatagtttag tggtaaagt gtgattcgtt ctattatccc    840
```

```
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aaggtcactt agacattgaa aaattggatt attaaattgc gaaacataat   1020
ttttgaattg gatcaatact tccaattgaa taagtatgaa taaggatcc atggatgaag    1080 atagaaagtt gatttctaat cgtaactaaa tcttcaattt cttatttgta aagaagaaag   1140
tgaagcaaaa tagctattaa acgatgactt tggtttacta gagacatcaa catattgttt   1200
tagctcggtg gaaacaaaat cctttcctc aggatcctat taaatagaaa tagagaacga   1260
aataactaga aaggttgtta gaatcccct cttctagaag gatcatctac aaagctattc    1320
gttttatctg tattcagatc aaaagctgac atagatgtta tgggtagaat tcttttttt    1380 tttctaattt tgttcacatc ttagatctat aaattgactc atctccataa aggagccgaa   1440
tggaaccaaa gtttcatgtt cggttttgaa ttagagacgt tcaaaataat gaatcgacgt   1500
cgactataac ccctagcctt ccaagctaac gatgcgggtt cgattcccgc tacccgctct   1560
ctatctattt attctaaata ttttaatctt ttcattaaat caaatttagt ttattagtat   1620
tagtacatca ttgaatatac aattc                                          1645
```

<210> SEQ ID NO 3
<211> LENGTH: 1645
<212> TYPE: DNA
<213> ORGANISM: Ningqi No.3 (L. barbarum Linn)

<400> SEQUENCE: 3

```
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt cttctctct    240 tttcttcttt actatattat atagatatgt acaactttta tcatcaattt cctttatctc    300
tttatctaaa gtaaaggaag ggctcagaag agccaagaat atcaagaaaa ataaagaaga    360 ccgctttttct ttgtcttgat tttgttcgaa aggaccctct tattctcatg gcctggtctg    420
gtcagtaccc agccgggcct ctttttgttcc aacgaatttg aatttgaaaa caaaaatgcc    480
tgttatagtt gtaatatttc atttttaattg aatagttaat attcaagcaa caagaaaaaa    540
ttcccatttt tgctaaaagt aaaaaaaata tatatgaa atagaaaatt cgatcaaaat    600
aaaagtctca tttctctttc tgctttttta tgtttaccat cttgctggac taaaaaaag    660 aagctttcga gtattccaca atgcattttt atgttatgat tttagtggtt ttgacgaccc    720
tatcttatcc tatcttgatt accacaattc ccctgttcga caaaagttgc atttgtatac    780
aataatcgaa ttgtagcggg tatagtttag tggtaaaagt gtgattcgtt ctattatccc    840
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aaggtcactt agacattgaa aaattggatt attaaattgc gaaacataat   1020
ttttgaattg gatcaatact tccaattgaa taagtatgaa taaggatcc atggatgaag    1080 atagaaagtt gatttctaat cgtaactaaa tcttcaattt cttatttgta aagaagaaag   1140
tgaagcaaaa tagctattaa acgatgactt tggtttacta gagacatcaa catattgttt   1200
tagctcggtg gaaacaaaat cctttcctc aggatcctat taaatagaaa tagagaacga   1260
```

| | | |
|---|---|---|
| aataactaga aaggttgtta gaatccccct cttctagaag gatcatctac aaagctattc | 1320 | |
| gttttatctg tattcagatc aaaagctgac atagatgtta tgggtagaat tcttttttt | 1380 | |
| tttctaattt tgttcacatc ttagatctat aaattgactc atctccataa aggagccgaa | 1440 | |
| tgaaaccaaa gtttcatgtt cggttttgaa ttagagacgt tcaaaataat gaatcgacgt | 1500 | |
| cgactataac ccctagcctt ccaagctaac gatgcgggtt cgattcccgc tacccgctct | 1560 | |
| ctatctattt attctaaata ttttaatctt ttcattaaat caaatttagt ttattagtat | 1620 | |
| tagtacatca ttgaatatac aattc | 1645 | |

<210> SEQ ID NO 4
<211> LENGTH: 1646
<212> TYPE: DNA
<213> ORGANISM: Ningqi No.4 (L. barbarum Linn)

<400> SEQUENCE: 4

| | | |
|---|---|---|
| ttaggatttg gtctattcca cacatttaac taagaataag aacaaaggat ttcgaaaatt | 60 | |
| gaaaaaaaaa atcaagtcat caacggaaag agagggattc gaaccctcgg tacgattaac | 120 | |
| tcgtacaacg gattagcaat ccgccgcttt agtccactca gccatctctc ccaattgaaa | 180 | |
| aagataatta ctacatgaga tagcacataa gataaaggaa agaatctttc tttctctctt | 240 | |
| ttcttcttta ctatattata tagatatgta caacttttat catcaatttc ctttatctct | 300 | |
| ttatctaaag taaaggaagg gctcagaaga gccaagaata tcaagaaaaa taagaagac | 360 | |
| cgcttttctt tgtcttgatt tgttcgaaa ggaccctctt attctcatgg cctggtctgg | 420 | |
| tcagtaccca gccgggcctc ttttgttcca acgaatttga atttgaaaac aaaaatgcct | 480 | |
| gttatagttg taatatttca ttttaattga atagttaata ttcaagcaac aagaaaaaat | 540 | |
| tcccatttt gctaaaagta aaaaaatat atatatgaaa tagaaaattc gatcaaaata | 600 | |
| aaagtctcat ttctctttct gctttttat gtttaccatc ttgctggact aaaaaaaga | 660 | |
| agctttcgag tattccacaa tgcattttta tgttatgatt ttagtggttt tgacgaccct | 720 | |
| atcttatcct atcttgatta ccacaattcc cctgttcgac aaaagttgca tttgtataca | 780 | |
| ataatcgaat tgtagcgggt atagtttagt ggtaaaagtg tgattcgttc tattatccct | 840 | |
| taaatagtta aagggtcctt cggtttgatt cgtattccga tcaaaaactt tatttcttaa | 900 | |
| aaggattaaa tccttttcct ctcaatgaca gattcgagaa caaatacaca ttctcgtgat | 960 | |
| ttgtatccaa aggtcactta gacattgaaa aattggatta ttaaattgcg aaacataatt | 1020 | |
| tttgaattgg atcaatactt ccaattgaat aagtatgaat aaaggatcca tggatgaaga | 1080 | |
| tagaaagttg atttctaatc gtaactaaat cttcaatttc ttatttgtaa agaagaaagt | 1140 | |
| gaagcaaaat agctattaaa cgatgacttt ggtttactag agacatcaac atattgtttt | 1200 | |
| agctcggtgg aaacaaaatc cttttcctca ggatcctatt aaatagaaat agagaacgaa | 1260 | |
| ataactagaa aggttgttag aatcccctc ttctagaagg atcatctaca aagctattcg | 1320 | |
| ttttatctgt attcagacca aaagctgaca tagatgttat gggtagaatt cttttttt | 1380 | |
| ttttctaatt tgttcacat cttagatcta taaattgact catctccata aaggagccga | 1440 | |
| atgaaaccaa gtttcatgt tcggttttga attagagacg tcaaaataa tgaatcgacg | 1500 | |
| tcgactataa ccctagcct tccaagctaa cgatgcgggt tcgattcccg ctacccgctc | 1560 | |
| tctatctatt tattctaaat attttaatct tttcattaaa tcaaatttag tttattagta | 1620 | |
| ttagtacatc attgaatata caattc | 1646 | |

<210> SEQ ID NO 5
<211> LENGTH: 1645
<212> TYPE: DNA
<213> ORGANISM: Ningqi No.5 (L. barbarum Linn)

<400> SEQUENCE: 5

| | | | | | |
|---|---|---|---|---|---|
| ttaggatttg | gtctattcca | cacatttaac | taagaataag | aacaaaggat | ttcgaaaatt | 60 |
| gaaaaaaaaa | aatcaagtca | tcaacggaaa | gagagggatt | cgaaccctcg | gtacgattaa | 120 |
| ctcgtacaac | ggattagcaa | tccgccgctt | tagtccactc | agccatctct | cccaattgaa | 180 |
| aaagataatt | actacatgag | atagcacata | agataaagga | aagaatcttt | ctttctctct | 240 |
| tttcttcttt | actatattat | atagatatgt | acaacttttta | tcatcaattt | cctttatctc | 300 |
| tttatctaaa | gtaaaggaag | ggctcagaag | agccaagaat | atcaagaaaa | ataaagaaga | 360 |
| ccgcttttct | ttgtcttgat | tttgttcgaa | aggaccctct | tattctcatg | gcctggtctg | 420 |
| gtcagtaccc | agccgggcct | cttttgttcc | aacgaatttg | aatttgaaaa | caaaaatgcc | 480 |
| tgttatagtt | gtaatatttc | attttaattg | aatagttaat | attcaagcaa | caagaaaaaa | 540 |
| ttcccatttt | tgctaaaagt | aaaaaaaata | tatatgaa | atagaaaatt | cgatcaaaat | 600 |
| aaagtctca | tttctcttc | tgcttttta | tgtttaccat | cttgctggac | taaaaaaag | 660 |
| aagctttcga | gtattccaca | atgcatttt | atgttatgat | tttagtggtt | ttgacgaccc | 720 |
| tatcttatcc | tatcttgatt | accacaattc | ccctgttcga | caaagttgc | atttgtatac | 780 |
| aataatcgaa | ttgtagcggg | tatagtttag | tggtaaaagt | gtgattcgtt | ctattatccc | 840 |
| ttaaatagtt | aaagggtcct | tcggtttgat | tcgtattccg | atcaaaaact | ttatttctta | 900 |
| aaaggattaa | atccttttcc | tctcaatgac | agattcgaga | acaaatacac | attctcgtga | 960 |
| tttgtatcca | aggtcactt | agacattgaa | aaattggatt | attaaattgc | gaaacataat | 1020 |
| ttttgaattg | gatcaatact | tccaattgaa | taagtatgaa | taaggatcc | atggatgaag | 1080 |
| atagaaagtt | gatttctaat | cgtaactaaa | tcttcaattt | cttatttgta | aagaagaaag | 1140 |
| tgaagcaaaa | tagctattaa | acgatgactt | tggtttacta | gagacatcaa | catattgttt | 1200 |
| tagctcggtg | gaaacaaaat | ccttttcctc | aggatcctat | taaatagaaa | tagagaacga | 1260 |
| aataactaga | aaggttgtta | gaatcccct | cttctagaag | gatcatctac | aaagctattc | 1320 |
| gttttatctg | tattcagatc | aaaagctgac | atagatgtta | tgggtagaat | tcttttttt | 1380 |
| tttctaattt | tgttcacatc | ttagatctat | aaattgactc | atctccataa | aggagccgaa | 1440 |
| tgaaaccaaa | gtttcatgtt | cggttttgaa | ttagagacgt | tcaaaataat | gaatcgacgt | 1500 |
| cgactataac | ccctagcctt | ccaagctaac | gatgcgggtt | cgattcccgc | tacccgctct | 1560 |
| ctatctatt | attctaaata | ttttaatctt | ttcattaaat | caaatttagt | ttattagtat | 1620 |
| tagtacatca | ttgaatatac | aattc | | | | 1645 |

<210> SEQ ID NO 6
<211> LENGTH: 1644
<212> TYPE: DNA
<213> ORGANISM: Ningqi No.6 (L. barbarum Linn)

<400> SEQUENCE: 6

| | | | | | |
|---|---|---|---|---|---|
| ttaggatttg | gtctattcca | cacatttaac | taagaataag | aacaaaggat | ttcgaaaatt | 60 |
| gaaaaaaaaa | aatcaagtca | tcaacggaaa | gagagggatt | cgaaccctcg | gtacgattaa | 120 |
| ctcgtacaac | ggattagcaa | tccgccgctt | tagtccactc | agccatctct | cccaattgaa | 180 |
| aaagataatt | actacatgag | atagcacata | agataaagga | aagaatcttt | ctttctctct | 240 |

```
tttcttcttt actatattat atagatatgt acaactttta tcatcaattt cctttatctc    300
tttatctaaa gtaaaggaag ggctcagaag agccaagaat atcaagaaaa ataaagaaga    360
ccgcttttct ttgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc attttaattg aatagttaat attcaagcaa caagaaaaaa    540
ttcccatttt tgctaaaagt aaaaaaaata tatatgaa atagaaaatt cgatcaaaat    600
aaaagtctca tttctctttc tgcttttta tgtttaccat cttgctggac taaaaaaaag    660
aagctttcga gtattccaca atgcattttt atgttatgat tttagtggtt ttgacgaccc    720
tatcttatcc tatcttgatt accacaattc ccctgttcga caaaagttgc atttgtatac    780
aataatcgaa ttgtagcggg tatagtttag tggtaaaagt gtgattcgtt ctattatccc    840
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aaggtcactt agacattgaa aaattggatt attaaattgc gaaacataat   1020
ttttgaattg gatcaatact tccaattgaa taagtatgaa taaggatcc atggatgaag   1080 atagaaagtt gatttctaat cgtaactaaa tcttcaattt cttatttgta aagaagaaag   1140
tgaagcaaaa tagctattaa acgatgactt tggtttacta gagacatcaa catattgttt   1200
tagctcggtg gaaacaaaat ccttttcctc aggatcctat taatagaaa tagagaacga   1260 aataactaga aaggttgtta gaatccccct cttctagaag gatcatctac aaagctattc   1320
gttttatctg tattcagatc aaagctgac atagatgtta tgggtagaat tcttttttt   1380 ttctaatttt gttcacatct tagatctata aattgactca tctccataaa ggagccgaat   1440
gaaaccaaag tttcatgttc ggttttgaat tagagacgtt caaaataatg aatcgacgtc   1500
gactataacc cctagccttc caagctaacg atgcgggttc gattcccgct acccgctctc   1560
tatctattta ttctaaatat tttaatcttt tcattaaatc aaatttagtt tattagtatt   1620
agtacatcat tgaatataca attc                                         1644
```

<210> SEQ ID NO 7
<211> LENGTH: 1645
<212> TYPE: DNA
<213> ORGANISM: Ningqi No.7 (L. barbarum Linn)

<400> SEQUENCE: 7

```
ttaggatttg gtctattcca cacatttaac taagaataag acaaaggat ttcgaaaatt     60 gaaaaaaaaa aatcaagtca tcaacggaaa gagagggatt cgaaccctcg gtacgattaa   120
ctcgtacaac ggattagcaa tccgccgctt tagtccactc agccatctct cccaattgaa   180
aaagataatt actacatgag atagcacata agataaagga aagaatcttt ctttctctct   240
tttcttcttt actatattat atagatatgt acaactttta tcatcaattt cctttatctc   300
tttatctaaa gtaaaggaag ggctcagaag agccaagaat atcaagaaaa ataaagaaga   360
ccgcttttct ttgtcttgat tttgttcgaa aggaccctct tattctcatg gcctggtctg   420
gtcagtaccc agccgggcct cttttgttcc aacgaatttg aatttgaaaa caaaaatgcc   480
tgttatagtt gtaatatttc attttaattg aatagttaat attcaagcaa caagaaaaaa   540
ttcccatttt tgctaaaagt aaaaaaaata tatatgaa atagaaaatt cgatcaaaat   600
aaaagtctca tttctctttc tgcttttta tgtttaccat cttgctggac taaaaaaaag   660
aagctttcga gtattccaca atgcattttt atgttatgat tttagtggtt ttgacgaccc   720
```

| | |
|---|---|
| tatcttatcc tatcttgatt accacaattc ccctgttcga caaaagttgc atttgtatac | 780 |
| aataatcgaa ttgtagcggg tatagtttag tggtaaaagt gtgattcgtt ctattatccc | 840 |
| ttaaatagtt aaagggtcct tcggtttgat tcgtattccg atcaaaaact ttatttctta | 900 |
| aaaggattaa atccttttcc tctcaatgac agattcgaga caaatacac attctcgtga | 960 |
| tttgtatcca aaggtcactt agacattgaa aaattggatt attaaattgc gaaacataat | 1020 |
| ttttgaattg gatcaatact tccaattgaa taagtatgaa taaggatcc atggatgaag | 1080 |
| atagaaagtt gatttctaat cgtaactaaa tcttcaattt cttatttgta aagaagaaag | 1140 |
| tgaagcaaaa tagctattaa acgatgactt tggtttacta gagacatcaa catattgttt | 1200 |
| tagctcggtg aaacaaaat ccttttcctc aggatcctat aaatagaaa tagagaacga | 1260 |
| aataactaga aaggttgtta gaatccccct cttctagaag gatcatctac aaagctattc | 1320 |
| gttttatctg tattcagatc aaaagctgac atagatgtta tgggtagaat tcttttttt | 1380 |
| tttctaattt tgttcacatc ttagatctat aaattgactc atctccataa aggagccgaa | 1440 |
| tgaaaccaaa gtttcatgtt cggttttgaa ttagagacgt tcaaaataat gaatcgacgt | 1500 |
| cgactataac ccctagcctt ccaagctaac gatgcgggtt cgattcccgc tacccgctct | 1560 |
| ctatctattt attctaaata ttttaatctt ttcattaaat caaatttagt ttattagtat | 1620 |
| tagtacatca ttgaatatac aattc | 1645 |

<210> SEQ ID NO 8
<211> LENGTH: 1645
<212> TYPE: DNA
<213> ORGANISM: L. barbarum Linn

<400> SEQUENCE: 8

| | |
|---|---|
| ttaggatttg gtctattcca cacatttaac taagaataag aacaaaggat ttcgaaaatt | 60 |
| gaaaaaaaaa aatcaagtca tcaacggaaa gagagggatt cgaaccctcg gtacgattaa | 120 |
| ctcgtacaac ggattagcaa tccgccgctt tagtccactc agccatctct cccaattgaa | 180 |
| aaagataatt actacatgag atagcacata agataaagga aagaatcttt ctttctctct | 240 |
| tttcttcttt actatattat atagatatgt acaacttta tcatcaattt cctttatctc | 300 |
| tttatctaaa gtaaaggaag ggctcagaag agccaagaat atcaagaaaa ataaagaaga | 360 |
| ccgcttttct ttgtcttgat tttgttcgaa aggaccctct tattctcatg gcctggtctg | 420 |
| gtcagtaccc agccgggcct cttttgttcc aacgaatttg aatttgaaaa caaaaatgcc | 480 |
| tgttatagtt gtaatatttc attttaattg aatagttaat attcaagcaa caagaaaaaa | 540 |
| ttcccatttt tgctaaaagt aaaaaaaata tatatgaa atagaaaatt cgatcaaaat | 600 |
| aaaagtctca tttctctttc tgcttttta tgtttaccat cttgctggac taaaaaaag | 660 |
| aagctttcga gtattccaca atgcattttt atgttatgat tttagtggtt ttgacgaccc | 720 |
| tatcttatcc tatcttgatt accacaattc ccctgttcga caaaagttgc atttgtatac | 780 |
| aataatcgaa ttgtagcggg tatagtttag tggtaaaagt gtgattcgtt ctattatccc | 840 |
| ttaaatagtt aaagggtcct tcggtttgat tcgtattccg atcaaaaact ttatttctta | 900 |
| aaaggattaa atccttttcc tctcaatgac agattcgaga caaatacac attctcgtga | 960 |
| tttgtatcca aaggtcactt agacattgaa aaattggatt attaaattgc gaaacataat | 1020 |
| ttttgaattg gatcaatact tccaattgaa taagtatgaa taaggatcc atggatgaag | 1080 |
| atagaaagtt gatttctaat cgtaactaaa tcttcaattt cttatttgta aagaagaaag | 1140 |

```
tgaagcaaaa tagctattaa acgatgactt tggtttacta gagacatcaa catattgttt   1200
tagctcggtg gaaacaaaat ccttttcctc aggatcctat aaatagaaaa tagagaacga   1260
aataactaga aaggttgtta gaatcccccct cttctagaag gatcatctac aaagctattc   1320
gttttatctg tattcagatc aaaagctgac atagatgtta tgggtagaat tcttttttt    1380 tttctaattt tgttcacatc ttagatctat aaattgactc atctccataa aggagccgaa   1440
tgaaaccaaa gtttcatgtt cggttttgaa ttagagacgt tcaaaataat gaatcgacgt   1500
cgactataac ccctagcctt ccaagctaac gatgcgggtt cgattcccgc tacccgctct   1560
ctatctattt attctaaata ttttaatctt ttcattaaat caaatttagt ttattagtat   1620
tagtacatca ttgaatatac aattc                                         1645

<210> SEQ ID NO 9
<211> LENGTH: 1646
<212> TYPE: DNA
<213> ORGANISM: L. barbarum Linn. var. auranticarpum K.F.Ching var. nov.

<400> SEQUENCE: 9
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt ctatattata tagatatgta caacttttat catcaatttc ctttatctct    300
ttatctaaag taaaggaagg gctcagaaga gccaagaata tcaagaaaaa taagaagac    360 cgcttttctt tgtcttgatt ttgttcgaaa ggaccctctt attctcatgg cctggtctgg    420 tcagtacccca gccgggcctc ttttgttcca acgaatttga atttgaaaac aaaaatgcct    480
gttatagttg taatatttca tattaattga atagttaata ttcaagcaac aagaaaaaat    540
tcccattttt gctaaaagta aaaaaaaaat atatatgaaa tagaaaattc gatcaaaata    600
aaagtctcat ttctctttct gcttttttat gtttaccatc ttgctggact aaaaaaaaga    660
agctttcgag tattccacaa tgcatttttta tgttatgatt ttagtggttt tgacgaccct    720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
aaggatttaa tccttttcct ctcaatgaca gattcgagaa caaatacaca ttctcgtgat    960
ttgtatccaa aggtcactta gacattgaaa aattggatta tgaaattgcg aaacataatt   1020
tttgaattgg atcaatactt ccaattgaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc cttttcctca ggatcctatt aaatagaaat agagaacgaa   1260
ataactagaa aggttgttag aatcccccctc ttctagaagg atcatctaca aagctattcg   1320
ttttatctgt attcagacca aaagctgaca tagatgttat gggtagaatt cttttttttt   1380
ttttctaatt ttgttcacat cttagatcta taaattgact catctccata aggagccga    1440 atgaaaccaa agtttcatgt tcggttttga attagagacg ttcaaaataa tgaatcgacg   1500
tcgactataa ccctagcct tccaagctaa cgatgcgggt tcgattcccg ctacccgctc    1560
tctaaatatt tattctaaat atttagatct tttcattaaa tcaaatttag tttattagta   1620
```

```
ttagtacatc attgaatata caattc                                      1646
```

<210> SEQ ID NO 10
<211> LENGTH: 1645
<212> TYPE: DNA
<213> ORGANISM: Mengqi 1L. barbarum

<400> SEQUENCE: 10

```
ttaggatttg gtctattcca cacatttaac taagaataag aacaaaggat ttcgaaaatt    60
gaaaaaaaaa aatcaagtca tcaacggaaa gagagggatt cgaaccctcg gtacgattaa   120
ctcgtacaac ggattagcaa tccgccgctt tagtccactc agccatctct cccaattgaa   180
aaagataatt actacatgag atagcacata agataaagga agaatctttt ctttctctct   240
tttcttcttt actatattat atagatatgt acaacttttta tcatcaattt cctttatctc   300
tttatctaaa gtaaaggaag ggctcagaag agccaagaat atcaagaaaa ataagaaga   360
ccgcttttct ttgtcttgat tttgttcgaa aggaccctct tattctcatg gcctggtctg   420
gtcagtaccc agccgggcct cttttgttcc aacgaatttg aatttgaaaa caaaaatgcc   480
tgttatagtt gtaatatttc attttaattg aatagttaat attcaagcaa caagaaaaaa   540
ttcccatttt tgctaaaagt aaaaaaaata tatatgaa atagaaaatt cgatcaaaat   600
aaaagtctca tttctctttc tgcttttta tgtttaccat cttgctggac taaaaaaaag   660
aagctttcga gtattccaca atgcattttt atgttatgat tttagtggtt ttgacgaccc   720
tatcttatcc tatcttgatt accacaattc ccctgttcga caaagttgc atttgtatac   780
aataatcgaa ttgtagcggg tatagtttag tggtaaaagt gtgattcgtt ctattatccc   840
ttaaatagtt aaagggtcct tcggtttgat tcgtattccg atcaaaaact ttatttctta   900
aaaggattaa atccttttcc tctcaatgac agattcgaga acaaatacac attctcgtga   960
tttgtatcca aaggtcactt agacattgaa aaattggatt attaaattgc gaaacataat  1020
ttttgaattg gatcaatact tccaattgaa taagtatgaa taaggatcc atggatgaag  1080
atagaaagtt gatttctaat cgtaactaaa tcttcaattt cttatttgta agaagaaag  1140
tgaagcaaaa tagctattaa acgatgactt tggtttacta gagacatcaa catattgttt  1200
tagctcggtg gaaacaaaat ccttttcctc aggatcctat taaatagaaa tagaaacga  1260
aataactaga aaggttgtta gaatccccct cttctagaag gatcatctac aaagctattc  1320
gttttatctg tattcagatc aaaagctgac atagatgtta tgggtagaat tctttttttt  1380
tttctaattt tgttcacatc ttagatctat aaattgactc atctccataa aggagccgaa  1440
tgaaaccaaa gtttcatgtt cggttttgaa ttagagacgt tcaaaataat gaatcgacgt  1500
cgactataac ccctagcctt ccaagctaac gatgcgggtt cgattcccgc tacccgctct  1560
ctatctattt attctaaata ttttaatctt ttcattaaat caaatttagt ttattagtat  1620
tagtacatca ttgaatatac aattc                                        1645
```

<210> SEQ ID NO 11
<211> LENGTH: 1645
<212> TYPE: DNA
<213> ORGANISM: Lycium barbarum Bianguo

<400> SEQUENCE: 11

```
ttaggatttg gtctattcca cacatttaac taagaataag aacaaaggat ttcgaaaatt    60
gaaaaaaaaa aatcaagtca tcaacggaaa gagagggatt cgaaccctcg gtacgattaa   120
```

```
ctcgtacaac ggattagcaa tccgccgctt tagtccactc agccatctct cccaattgaa      180
aaagataatt actacatgag atagcacata agataaagga aagaatcttt ctttctctct      240
tttcttcttt actatattat atagatatgt acaacttttta tcatcaattt cctttatctc     300
tttatctaaa gtaaaggaag ggctcagaag agccaagaat atcaagaaaa ataaagaaga      360
ccgcttttct ttgtcttgat tttgttcgaa aggaccctct tattctcatg gcctggtctg      420
gtcagtaccc agccgggcct cttttgttcc aacgaatttg aatttgaaaa caaaaatgcc      480
tgttatagtt gtaatatttc attttaattg aatagttaat attcaagcaa caagaaaaaa      540
ttcccatttt tgctaaaagt aaaaaaaata tatatgaaa atagaaaatt cgatcaaaat       600
aaaagtctca tttctctttc tgcttttttta tgtttaccat cttgctggac taaaaaaaag     660
aagcttcga gtattccaca atgcattttt atgttatgat tttagtggtt ttgacgaccc       720
tatcttatcc tatcttgatt accacaattc ccctgttcga caaaagttgc atttgtatac      780
aataatcgaa ttgtagcggg tatagtttag tggtaaaagt gtgattcgtt ctattatccc      840
ttaaatagtt aaagggtcct tcggtttgat tcgtattccg atcaaaaact ttatttctta     900
aaaggattaa atccttttcc tctcaatgac agattcgaga acaaatacac attctcgtga     960
tttgtatcca aaggtcactt agacattgaa aaattggatt attaaattgc gaaacataat     1020
ttttgaattg gatcaatact tccaattgaa taagtatgaa taaaggatcc atggatgaag    1080
atagaaagtt gatttctaat cgtaactaaa tcttcaatttt cttatttgta aagaagaaag   1140
tgaagcaaaa tagctattaa acgatgactt tggtttacta gagacatcaa catattgttt    1200
tagctcggtg gaaacaaaat ccttttcctc aggatcctat taaatagaaa tagagaacga    1260
aataactaga aaggttgtta gaatccccct cttctagaag gatcatctac aaagctattc    1320
gttttatctg tattcagatc aaaagctgac atagatgtta tgggtagaat tcttttttt     1380
tttctaattt tgttcacatc ttagatctat aaattgactc atctccataa aggagccgaa    1440
tgaaaccaaa gttcatgtt cggttttgaa ttagagacgt tcaaaataat gaatcgacgt     1500
cgactataac ccctagcctt ccaagctaac gatgcgggtt cgattcccgc tacccgctct    1560
ctatctattt attctaaata ttttaatctt ttcattaaat caaatttagt ttattagtat    1620
tagtacatca ttgaatatac aattc                                           1645
```

<210> SEQ ID NO 12
<211> LENGTH: 1645
<212> TYPE: DNA
<213> ORGANISM: Lycium ruthenicum Murr.

<400> SEQUENCE: 12

```
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt ctatattata tagatatgta caacttttat catcaatttc ctttatctct    300
ttatctaaag taaaggaagg gctcagaaga gccaagaata tcaagaaaaa taagaagac     360
cgcttttctt tgtcttgatt tgttcgaaa ggaccctctt attctcatgg cctggtctgg     420
tcagtaccca gccgggcctc ttttgttcca acgaatttga atttgaaaac aaaaatgcct    480
gttatagttg taatatttca tattaattga atagttaata ttcaagcaac aagaaaaaat    540
tcccatttt gctaaaagta aaaaaaaaat atatatgaaa tagaaaattc gatcaaaata     600
```

-continued

```
aaagtctcat ttctctttct gcttttttat gtttaccatc ttgctggact aaaaaaaaga      660
agctttcgag tattccacaa tgcattttta tgttatgatt ttagtggttt tgacgaccct      720
atcttatcct atcttgatta ccacaattcc cctgttcgac aaaagttgca tttgtataca      780
ataatcgaat tgtagcgggt atagtttagt ggtaaaagtg tgattcgttc tattatccct      840
taaatagtta aagggtcctt cggtttgatt cgtattccga tcaaaaactt tatttcttaa      900
aaggatttaa tccttttcct ctcaatgaca gattcgagaa caaatacaca ttctcgtgat      960
ttgtatccaa aggtcactta gacattgaaa aattggatta tgaaattgcg aaacataatt     1020
tttgaattgg atcaatactt ccaattgaat aagtatgaat aaaggatcca tggatgaaga     1080
tagaaagttg atttctaatc gtaactaaat cttcaatttc ttatttgtaa agaagaaagt     1140
gaagcaaaat agctattaaa cgatgacttt ggtttactag agacatcaac atattgtttt     1200
agctcggtgg aaacaaaatc cttttcctca ggatcctatt aaatagaaat agagaacgaa     1260
ataactagaa aggttgttag aatccccctc ttctagaagg atcatctaca aagctattcg     1320
ttttatctgt attcagacca aaagctgaca tagatgttat gggtagaatt cttttttttt     1380
tttctaattt tgttcacatc ttagatctat aaattgactc atctccataa aggagccgaa     1440
tgaaaccaaa gtttcatgtt cggttttgaa ttagagacgt tcaaaataat gaatcgacgt     1500
cgactataac ccctagcctt ccaagctaac gatgcgggtt cgattcccgc tacccgctct     1560
ctaaatattt attctaaata tttagatctt ttcattaaat caaatttagt ttattagtat     1620
tagtacatca ttgaatatac aattc                                            1645
```

<210> SEQ ID NO 13
<211> LENGTH: 1645
<212> TYPE: DNA
<213> ORGANISM: lycium

<400> SEQUENCE: 13

```
ttaggatttg gtctattcca cacatttaac taagaataag aacaaaggat ttcgaaaatt       60
gaaaaaaaaa aatcaagtca tcaacggaaa gagagggatt cgaaccctcg gtacgattaa      120
ctcgtacaac ggattagcaa tccgccgctt tagtccactc agccatctct cccaattgaa      180
aaagataatt actacatgag atagcacata agataaagga aagaatcttt ctttctctct      240
tttcttcttt actatattat atagatatgt acaacttttta tcatcaattt cctttatctc      300
tttatctaaa gtaaggaag ggctcagaag agccaagaat atcaagaaaa ataagaagaa       360
ccgcttttct ttgtcttgat tttgttcgaa aggaccctct tattctcatg gcctggtctg      420
gtcagtaccc agccgggcct cttttgttcc aacgaatttg aatttgaaaa caaaaatgcc      480
tgttatagtt gtaatatttc attttaattg aatagttaat attcaagcaa caagaaaaaa      540
ttcccatttt tgctaaaagt aaaaaaaata tatatgaa atagaaaatt cgatcaaaat       600
aaaagtctca tttctctttc tgcttttttta tgtttaccat cttgctggac taaaaaaaag      660
aagctttcga gtattccaca atgcattttt atgttatgat tttagtggtt tgacgaccc       720 tatcttatcc tatcttgatt accacaattc cctgttcga caaaagttgc atttgtatac       780
aataatcgaa ttgtagcggg tatagtttag tggtaaaagt gtgattcgtt ctattatccc      840
ttaaatagtt aaagggtcct tcggtttgat tcgtattccg atcaaaaact ttatttctta      900
aaaggattaa atccttttcc tctcaatgac agattcgaga acaaatacac attctcgtga      960
tttgtatcca aggtcactt agacattgaa aaattggatt attaaattgc gaaacataat     1020
```

```
ttttgaattg gatcaatact tccaattgaa taagtatgaa taaaggatcc atggatgaag      1080
atagaaagtt gatttctaat cgtaactaaa tcttcaattt cttatttgta aagaagaaag      1140
tgaagcaaaa tagctattaa acgatgactt tggtttacta gagacatcaa catattgttt      1200
tagctcggtg gaaacaaaat ccttttcctc aggatcctat taaatagaaa tagagaacga      1260
aataactaga aaggttgtta gaatccccct cttctagaag gatcatctac aaagctattc      1320
gttttatctg tattcagatc aaaagctgac atagatgtta tgggtagaat tcttttttt      1380 tttctaattt tgttcacatc ttagatctat aaattgactc atctccataa aggagccgaa      1440
tgaaaccaaa gtttcatgtt cggttttgaa ttagagacgt tcaaaataat gaatcgacgt      1500
cgactataac ccctagcctt ccaagctaac gatgcgggtt cgattcccgc tacccgctct      1560
ctatctattt attctaaata tttaatctt ttcattaaat caaatttagt ttattagtat      1620
tagtacatca ttgaatatac aattc                                           1645

<210> SEQ ID NO 14
<211> LENGTH: 1644
<212> TYPE: DNA
<213> ORGANISM: L. barbarum Linn

<400> SEQUENCE: 14
ttaggatttg gtctattcca cacatttaac taagaataag aacaaaggat ttcgaaaatt       60
gaaaaaaaaa aatcaagtca tcaacggaaa gagagggatt cgaaccctcg gtacgattaa      120
ctcgtacaac ggattagcaa tccgccgctt tagtccactc agccatctct cccaattgaa      180
aaagataatt actacatgag atagcacata agataaagga aagaatcttt ctttctctct      240
tttcttcttt ctatattata tagatatgta caacttttat catcaatttc ctttatctct      300
ttatctaaag taaaggaagg gctcagaaga gccaagaata tcaagaaaaa taagaagac       360 cgcttttctt tgtcttgatt ttgttcgaaa ggaccctctt attctcatgg cctggtctgg      420
tcagtaccca gccgggcctc ttttgttcca acgaatttga atttgaaaac aaaaatgcct      480
gttatagttg taatatttca tattaattga atagttaata ttcaagcaac aagaaaaaat      540
tcccattttt gctaaaagta aaaaaaaaat atatatgaaa tagaaaattc gatcaaaata      600
aaagtctcat ttctctttct gcttttttat gtttaccatc ttgctggact aaaaaaaaga      660
agctttcgag tattccacaa tgcattttta tgttatgatt ttagtggttt tgacgacccct     720 atcttatcct atcttgatta ccacaattcc cctgttcgac aaaagttgca tttgtataca      780
ataatcgaat tgtagcgggt atagtttagt ggtaaaagtg tgattcgttc tattatccct      840
taaatagtta aagggtcctt cggtttgatt cgtattccga tcaaaaactt tatttcttaa      900
aaggattaaa tccttttcct ctcaatgaca gattcgagaa caaatacaca ttctcgtgat      960
ttgtatccaa aggtcactta gacattgaaa aattggatta tgaaattgcg aaacataatt     1020
tttgaattgg atcaatactt ccaattaaat aagtatgaat aaaggatcca tggatgaaga     1080
tagaaagttg atttctaatc gtaactaaat cttcaatttc ttatttgtaa agaagaaagt     1140
gaagcaaaat agctattaaa cgatgacttt ggtttactag agacatcaac atattgtttt     1200
agctcggtgg aaacaaaatc cttttcctca ggatccatt aaatagaaat agagaacgaa      1260
ataactagaa aggttgttag aatcccctc ttctagaagg atcatctaca aagctattcg      1320
ttttatctgt attcagacca aaagctgaca tagatgttat gggtagaatt cttttttt      1380 ttctaatttt gttcacatct tagatctata aattgactca tctccataaa ggagccgaat     1440
gaaaccaaag tttcatgttc ggttttgaat tagagacgtt caaaataatg aatcgacgtc     1500
```

```
gactataacc cctagccttc caagctaacg atgcgggttc gattcccgct acccgctctc    1560
taaatattta ttctaaatat ttagatcttt tcattaaatc aaatttagtt tattagtatt    1620
agtacatcat tgaatataca attc                                          1644
```

<210> SEQ ID NO 15
<211> LENGTH: 1644
<212> TYPE: DNA
<213> ORGANISM: lycium

<400> SEQUENCE: 15

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga aagaatcttt ctttctctct     240
tttcttcttt ctatattata tagatatgta caacttttat catcaatttc ctttatctct     300
ttatctaaag taaggaagg gctcagaaga gccaagaata tcaagaaaaa taagaagac      360 cgcttttctt tgtcttgatt ttgttcgaaa ggaccctctt attctcatgg cctggtctgg     420
tcagtaccca gccgggcctc ttttgttcca acgaatttga atttgaaaac aaaaatgcct     480
gttatagttg taatatttca tattaattga atagttaata ttcaagcaac aagaaaaaat     540
tcccattttt gctaaaagta aaaaaaaaat atatatgaaa tagaaaattc gatcaaaata     600
aaagtctcat ttctctttct gcttttttat gtttaccatc ttgctggact aaaaaaaaga     660
agctttcgag tattccacaa tgcatttta tgttatgatt ttagtggttt tgacgaccct     720
atcttatcct atcttgatta ccacaattcc cctgttcgac aaaagttgca tttgtataca     780
ataatcgaat tgtagcgggt atagtttagt ggtaaaagtg tgattcgttc tattatccct     840
taaatagtta aagggtcctt cggtttgatt cgtattccga tcaaaaactt tatttcttaa     900
aaggattaaa tccttttcct ctcaatgaca gattcgagaa caaatacaca ttctcgtgat     960
ttgtatccaa aggtcactta gacattgaaa aattggatta tgaaattgcg aaacataatt    1020
tttgaattgg atcagtactt ccaattaaat aagtatgaat aaaggatcca tggatgaaga    1080
tagaaagttg atttctaatc gtaactaaat cttcaatttc ttatttgtaa agaagaaagt    1140
gaagcaaaat agctattaaa cgatgacttt ggtttactag agacatcaac atattgtttt    1200
agctcggtgg aaacaaaatc cttttcctca ggatcctatt aaatagaaat agagaacgaa    1260
ataactagaa aggttgttag aatcccctc ttctagaagg atcatctaca aagctattcg    1320
ttttatctgt attcagacca aaagctgaca tagatgttat gggtagaatt cttttttttt    1380 ttctaattt gttcacatct tagatctata aattgactca tctccataaa ggagccgaat    1440
gaaaccaaag tttcatgttc ggttttgaat tagagacgtt caaaataatg aatcgacgtc    1500
gactataacc cctagccttc caagctaacg atgcgggttc gattcccgct acccgctctc    1560
taaatattta ttctaaatat ttagatcttt tcattaaatc aaatttagtt tattagtatt    1620
agtacatcat tgaatataca attc                                          1644
```

<210> SEQ ID NO 16
<211> LENGTH: 1644
<212> TYPE: DNA
<213> ORGANISM: lycium

<400> SEQUENCE: 16

-continued

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga aagaatcttt ctttctctct     240
tttcttcttt ctatattata tagatatgta caacttttat catcaatttc ctttatctct     300
ttatctaaag taaggaagg gctcagaaga gccaagaata tcagaaaaaa taaagaagac      360
cgcttttctt tgtcttgatt tgttcgaaa ggaccctctt attctcatgg cctggtctgg      420
tcagtaccca gccgggcctc ttttgttcca acgaatttga atttgaaaac aaaaatgcct     480
gttatagttg taatatttca tattaattga atagttaata ttcaagcaac aagaaaaaat    540
tcccattttt gctaaaagta aaaaaaaaat atatatgaaa tagaaaattc gatcaaaata     600
aaagtctcat ttctctttct gctttttat gtttaccatc ttgctggact aaaaaaaga      660
agctttcgag tattccacaa tgcatttta tgttatgatt ttagtggttt tgacgaccct     720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
aaggattaaa tccttttcct ctcaatgaca gattcgagaa caaatacaca ttctcgtgat    960
ttgtatccaa aggtcactta gacattgaaa aattggatta tgaaattgcg aaacataatt   1020
tttgaattgg atcaatactt ccaattaaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc cttttcctca ggatcctatt aaatagaaat agagaacgaa   1260
ataactagaa aggttgttag aatccccctc ttctagaagg atcatctaca aagctattcg   1320
ttttatctgt attcagacca aaagctgaca tagatgttat gggtagaatt cttttttttt   1380
ttctaatttt gttcacatct tagatctata aattgactca tctccataaa ggagccgaat   1440
gaaaccaaag tttcatgttc ggttttgaat tagagacgtt caaataatg aatcgacgtc     1500
gactataacc cctagccttc caagctaacg atgcgggttc gattcccgct acccgctctc   1560
taaatattta ttctaaatat ttagatcttt tcattaaatc aaatttagtt tattagtatt   1620
agtacatcat tgaatataca attc                                           1644
```

<210> SEQ ID NO 17
<211> LENGTH: 1644
<212> TYPE: DNA
<213> ORGANISM: lycium

<400> SEQUENCE: 17

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga aagaatcttt ctttctctct     240
tttcttcttt ctatattata tagatatgta caacttttat catcaatttc ctttatctct     300
ttatctaaag taaggaagg gctcagaaga gccaagaata tcagaaaaaa taaagaagac      360
cgcttttctt tgtcttgatt tgttcgaaa ggaccctctt attctcatgg cctggtctgg      420
tcagtaccca gccgggcctc ttttgttcca acgaatttga atttgaaaac aaaaatgcct     480
```

```
gttatagttg taatatttca tattaattga atagttaata ttcaagcaac aagaaaaaat      540
tcccattttt gctaaaagta aaaaaaaaat atatatgaaa tagaaaattc gatcaaaata      600
aaagtctcat ttctctttct gctttttttat gtttaccatc ttgctggact aaaaaaaaga    660
agctttcgag tattccacaa tgcatttttta tgttatgatt ttagtggttt tgacgaccct    720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
aaggattaaa tccttttcct ctcaatgaca gattcgagaa caaatacaca ttctcgtgat    960
ttgtatccaa aggtcactta gacattgaaa aattggatta tgaaattgcg aaacataatt   1020
tttgaattgg atcaatactt ccaattaaat aagtatgaat aaaggatcca tgatgaaga    1080 tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc cttttcctca ggatcctatt aaatagaaat agagaacgaa   1260
ataactagaa aggttgttag aatcccctc ttctagaagg atcatctaca aagctattcg    1320
ttttatctgt attcagacca aaagctgaca tagatgttat gggtagaatt ctttttttt    1380 ttctaatttt gttcacatct tagatctata aattgactca tctccataaa ggagccgaat   1440
gaaaccaaag tttcatgttc ggttttgaat tagagacgtt caaaataatg aatcgacgtc   1500
gactataacc cctagccttc caagctaacg atgcgggttc gattcccgct actcgctctc   1560
taaatattta ttctaaatat ttagatcttt tcattaaatc aaatttagtt tattagtatt   1620
agtacatcat tgaatataca attc                                           1644
```

<210> SEQ ID NO 18
<211> LENGTH: 1644
<212> TYPE: DNA
<213> ORGANISM: lycium

<400> SEQUENCE: 18

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga agaatctttt ctttctctct    240
tttcttcttt ctatattata tagatatgta caacttttat catcaatttc ctttatctct    300
ttatctaaag taaaggaagg gctcagaaga gccaagaata tcaagaaaaa taaagaagac    360 cgctttttctt tgtcttgatt ttgttcgaaa ggaccctctt attctcatgg cctggtctgg   420
tcagtaccca gccgggcctc ttttgttcca acgaatttga atttgaaaac aaaaatgcct    480
gttatagttg taatatttca tattaattga atagttaata ttcaagcaac aagaaaaaat    540
tcccattttt gctaaaagta aaaaaaaaat atatatgaaa tagaaaattc gatcaaaata    600
aaagtctcat ttctctttct gctttttttat gtttaccatc ttgctggact aaaaaaaaga   660
agctttcgag tattccacaa tgcatttttta tgttatgatt ttagtggttt tgacgaccct   720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
```

```
aaggattaaa tccttttcct ctcaatgaca gattcgagaa caaatacaca ttctcgtgat    960
ttgtatccaa aggtcactta gacattgaaa aattggatta tgaaattgcg aaacataatt   1020
tttgaattgg atcaatactt ccaattaaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc ctttcctca ggatcctatt aaatagaaat agagaacgaa   1260
ataactagaa aggttgttag aatcccctc ttctagaagg atcatctaca aagctattcg   1320
ttttatctgt attcagacca aaagctgaca tagatgttat gggtagaatt cttttttttt   1380 ttctaattt gttcacatct tagatctata aattgactca tctccataaa ggagccgaat   1440
gaaaccaaag tttcatgttc ggttttgaat tagagacgtt caaaataatg aatcgacgtc   1500
gactataacc cctagccttc caagctaacg atgcgggttc gattcccgct acccgctctc   1560
taaatattta ttctaaatat ttagatcttt tcattaaatc aaatttagtt tattagtatt   1620
agtacatcat tgaatataca attc                                          1644
```

<210> SEQ ID NO 19
<211> LENGTH: 1643
<212> TYPE: DNA
<213> ORGANISM: lycium

<400> SEQUENCE: 19

```
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt ctatattata tagatatgta caacttttat catcaatttc ctttatctct    300
ttatctaaag taaaggaagg gctcagaaga gccaagaata tcaagaaaaa taagaagac     360 cgcttttctt tgtcttgatt ttgttcgaaa ggaccctctt attctcatgg cctggtctgg    420
tcagtaccca gccgggcctc ttttgttcca acgaatttga atttgaaaac aaaaatgcct    480
gttatagttg taatatttca tattaattga atagttaata ttcaagcaac aagaaaaaat    540
tcccattttt gctaaaagta aaaaaaaata tatatgaaat agaaaattcg atcaaaataa    600
aagtctcatt tctctttctg cttttttatg tttaccatct tgctggacta aaaaaaagaa    660
gctttcgagt attccacaat gcattttat gttatgattt tagtggtttt gacgaccta     720 tcttatccta tcttgattac cacaattccc ctgttcgaca aaagttgcat tgtatacaa     780 taatcgaatt gtagcgggta tagtttagtg gtaaaagtgt gattcgttct attatcccctt   840 aaatagttaa agggtccttc ggtttgattc gtattccgat caaaaacttt atttcttaaa    900
aggattaaat ccttttcctc tcaatgacag attcgagaac aaatacacat tctcgtgatt    960
tgtatccaaa ggtcacttag acattgaaaa attggattat gaaattgcga acataattt     1020 ttgaattgga tcaatacttc caattaaata agtatgaata aagggtccat ggatgaagat   1080
agaaagttga tttctaatcg taactaaatc ttcaatttct tatttgtaaa gaagaaagtg   1140
aagcaaaata gctattaaac gatgactttg gtttactaga gacatcaaca tattgtttta   1200
gctcggtgga aacaaaatcc ttttcctcag gatcctatta aatagaaata gagaacgaaa   1260
taactagaaa ggttgttaga atcccctctc tctagaagga tcatctacaa agctattcgt   1320
tttatctgta ttcagaccaa aagctgacat agatgttatg ggtagaattc tttttttttt   1380
```

```
tctaattttg ttcacatctt agatctataa attgactcat ctccataaag gagccgaatg    1440
aaaccaaagt ttcatgttcg gttttgaatt agagacgttc aaaataatga atcgacgtcg    1500
actataaccc ctagccttcc aagctaacga tgcgggttcg attcccgcta cccgctctct    1560
aaatatttat tctaaatatt tagatctttt cattaaatca aatttagttt attagtatta    1620
gtacatcatt gaatatacaa ttc                                            1643
```

<210> SEQ ID NO 20
<211> LENGTH: 1643
<212> TYPE: DNA
<213> ORGANISM: lycium

<400> SEQUENCE: 20

```
ttaggatttg gtctattcca cacatttaac taagaataag aacaaaggat ttcgaaaatt      60
gaaaaaaaaa aatcaagtca tcaacggaaa gagagggatt cggaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt ctatattata tagatatgta caacttttat catcaatttc ctttatctct    300
ttatctaaag taaggaagg gctcagaaga gccaagaata tcaagaaaaa taagaagac     360 cgcttttctt tgtcttgatt ttgttcgaaa ggaccctctt attctcatgg cctggtctgg    420
tcagtaccca gccgggcctc ttttgttcca acgaatttga atttgaaaac aaaaatgcct    480
gttatagttg taatatttca tattaattga atagttaata ttcaagcaac aagaaaaaat    540
tcccattttt gctaaaagta aaaaaaaaat atatatgaaa tagaaaattc gatcaaaata    600
aaagtctcat ttctctttct gcttttttat gtttaccatc ttgctggact aaaaaaaaga    660
agctttcgag tattccacaa tgcatttta tgttatgatt ttagtggttt tgacgaccct    720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
aaggattaaa tccttttcct ctcaatgaca gattcgagaa caaatacaca ttctcgtgat    960
ttgtatccaa aggtcactta gacattgaaa aattggatta tgaaattgcg aaacataatt   1020
tttgaattgg atcaatactt ccaattaaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgactt ggtttactag agcatcaac atattgtttt   1200 agctcggtgg aaacaaaatc cttttcctca ggatcctatt aaatagaaat agagaacgaa   1260
ataactagaa aggttgttag aatcccctc ttctagaagg atcatctaca aagctattcg   1320
ttttatctgt attcagacca aaagctgaca tagatgttat gggtagaatt ctttttttt    1380 tctaattttg ttcacatctt agatctataa attgactcat ctccataaag gagccgaatg   1440
aaaccaaagt ttcatgttcg gttttgaatt agagacgttc aaaataatga atcgacgtcg   1500
actataaccc ctagccttcc aagctaacga tgcgggttcg attcccgcta cccgctctct   1560
aaatatttat tctaaatatt tagatctttt cattaaacca aatttagttt attagtatta   1620
gtacatcatt gaatatacaa ttc                                           1643
```

<210> SEQ ID NO 21
<211> LENGTH: 1645
<212> TYPE: DNA

<213> ORGANISM: Lycium chinense MilL. var. potaninii (Pojark.) A. M. Lu

<400> SEQUENCE: 21

```
ttaggatttg gtctattcca cacatttaac taagaataag aacaaaggat ttcggaaatt      60
gaaaaaaaaa atcaagtcat caacggaaag agagggattc gaaccctcgg tacgattaac     120
tcgtacaacg gattagcaat ccgccgcttt agtccactca gccatctctc ccaattgaaa     180
aagataatta ctacatgaga tagcacataa gataaaggaa agaatctttc tttctctctt     240
ttcttcttta ctatattata tagatatgta caacttttat catcaatttc ctttatctct     300
ttatctaaag taaggaagg gctcagaaga gccaagaata tcaagaaaaa taagaagac       360
cgcttttctt tgtcttgatt tgttcgaaa ggaccctctt attctcatgg cctggtctgg      420
tcagtaccca gccgggcctc ttttgttcca acgaatttga atttgaaaac aaaaatgcct     480
gttatagttg taatatttca ttttaattga atagttaata ttcaagcaac aagaaaaaat    540
tcccattttt gctaaaagta aaaaaatat atatatgaaa tagaaaattc gatcaaaata     600
aaagtctcat ttctctttct gctttttat gtttaccatc ttgctggact aaaaaaaga      660
agctttcgag tattccacaa tgcattttta tgttatgatt ttagtggttt tgacgaccct    720
atcttatcct atcttgatta ccacaattcc cctgttcgac aaaagttgca tttgtataca    780
ataatcgaat tgtagcgggt atagtttagt ggtaaaagtg tgattcgttc tattatccct   840
taaatagtta aagggtcctt cggtttgatt cgtattccga tcaaaaactt tatttcttaa     900
aaggatttaa tcctttcct ctcaatgaca gattcgagaa caaatacaca ttctcgtgat     960
ttgtatccaa aggtcactta gacattgaaa aattggatta ttaaattgcg aaacataatt   1020
tttgaattgg atcaatactt ccaattgaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc cttttcctca ggatcctatt aaatagaaat agagaacgaa   1260
ataactagaa aggttgttag aatccccctc ttctagaagg atcatctaca aagctattcg   1320
ttttatctgt attcagacca aaagctgaca tagatgttat gggtagaatt cttttttttt   1380
tttctaattt tgttcacatc ttagatctat aaattgactc atctccataa aggagccgaa   1440
tgaaaccaaa gtttcatgtt cggttttgaa ttagagacgt tcaaaataat gaatcgacgt   1500
cgactataac ccctagcctt ccaagctaac gatgcgggtt cgattccgc tacccgctct    1560
ctatctattt attctaaata ttttaatctt ttcattaaat caaatttagt ttattagtat   1620
tagtacatca ttgaatatac aattc                                          1645
```

<210> SEQ ID NO 22
<211> LENGTH: 1645
<212> TYPE: DNA
<213> ORGANISM: lycium

<400> SEQUENCE: 22

```
ttaggatttg gtctattcca cacatttaac taagaataag aacaaaggat ttcgaaaatt      60
gaaaaaaaaa atcaagtcat caacggaaag agagggattc gaaccctcgg tacgattaac     120
tcgtacaacg gattagcaat ccgccgcttt agtccactca gccatctctc ccaattgaaa     180
aagataatta ctacatgaga tagcacataa gataaaggaa agaatctttc tttctctctt     240
ttcttcttta ctatattata tagatatgta caacttttat catcaatttc ctttatctct     300
ttatctaaag taaggaagg gctcagaaga gccaagaata tcaagaaaaa taagaagac       360
```

```
cgcttttctt tgtcttgatt ttgttcgaaa ggaccctctt attctcatgg cctggtctgg     420
tcagtaccca gccgggcctc ttttgttcca acgaatttga atttgaaaac aaaaatgcct     480
gttatagttg taatatttca ttttaattga atagttaata ttcaagcaac aagaaaaaat     540
tcccattttt gctaaaagta aaaaaaatat atatatgaaa tagaaaattc gatcaaaata     600
aaagtctcat ttctctttct gcttttttat gtttaccatc ttgctggact aaaaaaaaga     660
agctttcgag tattccacaa tgcatttta tgttatgatt ttagtggttt tgacgaccct     720
atcttatcct atcttgatta ccacaattcc cctgttcgac aaaagttgca tttgtataca     780
ataatcgaat gtagcgggt atagtttagt ggtaaaagtg tgattcgttc tattatccct     840
taaatagtta aagggtcctt cggtttgatt cgtattccga tcaaaaactt tatttcttaa     900
aaggattaaa tccttttcct ctcaatgaca gattcgagaa caaatacaca ttctcgtgat     960
ttgtatccaa aggtcactta gacattgaaa aattggatta ttaaattgcg aaacataatt    1020
tttgaattgg atcaatactt ccaattgaat aagtatgaat aaaggatcca tggatgaaga    1080
tagaaagttg atttctaatc gtaactaaat cttcaatttc ttatttgtaa agaagaaagt    1140
gaagcaaaat agctattaaa cgatgacttt ggtttactag agacatcaac atattgtttt    1200
agctcggtgg aaacaaaatc cttttcctca ggatcctatt aaatagaaat agagaacgaa    1260
ataactagaa aggttgttag aatcccctc ttctagaagg atcatctaca aagctattcg    1320
ttttatctgt attcagacca aaagctgaca tagatgttat gggtagaatt cttttttttt    1380
tttctaattt tgttcacatc ttagatctat aaattgactc atctccataa aggagccgaa    1440
tgaaaccaaa gtttcatgtt cggttttgaa ttagagacgt tcaaaataat gaatcgacgt    1500
cgactataac ccctagcctt ccaagctaac gatgcgggtt cgattcccgc tacccgctct    1560
ctatctattt attctaaata ttttaatctt ttcattaaat caaatttagt ttattagtat    1620
tagtacatca ttgaatatac aattc                                         1645
```

<210> SEQ ID NO 23
<211> LENGTH: 1645
<212> TYPE: DNA
<213> ORGANISM: lycium

<400> SEQUENCE: 23

```
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga agaatctttt ctttctctct     240
tttcttcttt actatattat atagatatgt acaacttta tcatcaattt cctttatctc     300
tttatctaaa gtaaaggaag ggctcagaag agccaagaat atcaagaaaa ataagaaga     360 ccgcttttct ttgtcttgat tttgttcgaa aggaccctct tattctcatg gcctggtctg     420
gtcagtaccc agccgggcct cttttgttcc aacgaatttg aatttgaaaa caaaaatgcc     480
tgttatagtt gtaatatttc attttaattg aatagttaat attcaagcaa caagaaaaaa     540
ttcccatttt tgctaaaagt aaaaaaaata tatatgaa atagaaaatt cgatcaaaat     600
aaaagtctca tttctctttc tgcttttta tgtttaccat cttgctggac taaaaaaaag     660
aagctttcga gtattccaca atgcattttt atgttatgat tttagtggtt ttgacgaccc     720
tatcttatcc tatcttgatt accacaattc ccctgttcga caaaagttgc atttgtatac     780
```

-continued

```
aataatcgaa ttgtagcggg tatagtttag tggtaaaagt gtgattcgtt ctattatccc      840
ttaaatagtt aaagggtcct tcggtttgat tcgtattccg atcaaaaact ttatttctta      900
aaaggattaa atccttttcc tctcaatgac agattcgaga acaaatacac attctcgtga      960
tttgtatcca aaggtcactt agacattgaa aaattggatt attaaattgc gaaacataat     1020
ttttgaattg gatcaatact tccaattgaa taagtatgaa taaggatcc  atggatgaag     1080 atagaaagtt gatttctaat cgtaactaaa tcttcaattt cttatttgta aagaagaaag     1140
tgaagcaaaa tagctattaa acgatgactt tggtttacta gagacatcaa catattgttt     1200
tagctcggtg gaaacaaaat cctttcctc aggatcctat taaatagaaa tagagaacga      1260
aataactaga aaggttgtta gaatccccct cttctagaag gatcatctac aaagctattc     1320
gttttatctg tattcagatc aaaagctgac atagatgtta tgggtagaat tcttttttttt   1380 tttctaattt tgttcacatc ttagatctat aaattgactc atctccataa aggagccgaa     1440
tgaaaccaaa gtttcatgtt cggttttgaa ttagagacgt tcaaaataat gaatcgacgt     1500
cgactataac ccctagcctt ccaagctaac gatgcgggtt cgattcccgc tacccgctct     1560
ctatctattt attctaaata ttttaatctt ttcattaaat caaatttagt ttattagtat     1620
tagtacatca ttgaatatac aattc                                           1645

<210> SEQ ID NO 24
<211> LENGTH: 1645
<212> TYPE: DNA
<213> ORGANISM: lycium

<400> SEQUENCE: 24
ttaggatttg gtctattcca cacatttaac taagaataag aacaaaggat ttcgaaaatt       60
gaaaaaaaaa aatcaagtca tcaacggaaa gagagggatt cgaaccctcg gtacgattaa      120
ctcgtacaac ggattagcaa tccgccgctt tagtccactc agccatctct cccaattgaa      180
aaagataatt actacatgag atagcacata agataaagga aagaatcttt ctttctctct      240
tttcttcttt actatattat atagatatgt acaacttta tcatcaattt cctttatctc       300
tttatctaaa gtaaaggaag ggctcagaag agccaagaat atcaagaaaa ataaagaaga      360 ccgctttttct ttgtcttgat tttgttcgaa aggaccctct tattctcatg gcctggtctg     420
gtcagtaccc agccgggcct cttttgttcc aacgaatttg aatttgaaaa caaaaatgcc      480
tgttatagtt gtaatatttc attttaattg aatagttaat attcaagcaa caagaaaaaa      540
ttcccatttt tgctaaaagt aaaaaaaata tatatgaa atagaaaatt cgatcaaaat       600 aaagtctca tttctctttc tgctttttta tgtttaccat cttgctggac taaaaaaag       660 aagctttcga gtattccaca atgcattttt atgttatgat tttagtggtt ttgacgaccc     720
tatcttatcc tatcttgatt accacaattc ccctgttcga caaaagttgc atttgtatac    780
aataatcgaa ttgtagcggg tatagtttag tggtaaaagt gtgattcgtt ctattatccc     840
ttaaatagtt aaagggtcct tcggtttgat tcgtattccg atcaaaaact ttatttctta     900
aaaggattaa atccttttcc tctcaatgac agattcgaga acaaatacac attctcgtga     960
tttgtatcca aaggtcactt agacattgaa aaattggatt attaaattgc gaaacataat    1020
ttttgaattg gatcaatact tccaattgaa taagtatgaa taaggatcc  gtggatgaag    1080 atagaaagtt gatttctaat cgtaactaaa tcttcaattt cttatttgta aagaagaaag    1140
tgaagcaaaa tagctattaa acgatgactt tggtttacta gagacatcaa catattgttt    1200
tagctcggtg gaaacaaaat cctttcctc aggatcctat taaatagaaa tagagaacga     1260
```

```
aataactaga aaggttgtta gaatccccct cttctagaag gatcatctac aaagctattc    1320
gttttatctg tattcagatc aaaagctgac atagatgtta tgggtagaat tcttttttt     1380 tttctaattt tgttcacatc ttagatctat aaattgactc atctccataa aggagccgaa    1440
tgaaaccaaa gtttcatgtt cggttttgaa ttagagacgt tcaaaataat gaatcgacgt    1500
cgactataac ccctagcctt ccaagctaac gatgcgggtt cgattcccgc tacccgctct    1560
ctatctattt attctaaata ttttaatctt ttcattaaat caaatttagt ttattagtat    1620
tagtacatca ttgaatatac aattc                                          1645
```

<210> SEQ ID NO 25
<211> LENGTH: 1645
<212> TYPE: DNA
<213> ORGANISM: Lycium chinense

<400> SEQUENCE: 25

```
ttaggatttg gtctattcca cacatttaac taagaataag aacaaaggat ttcgaaaatt     60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga aagaatcttt ctttctctct    240
tttcttcttt actatattat atagatatgt acaaccttta tcatcaattt cctttatctc    300
tttatctaaa gtaaaggaag ggctcagaag agccaagaat atcaagaaaa ataaagaaga    360
ccgcttttct ttgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc atttttaattg aatagttaat attcaagcaa caagaaaaaa    540
ttcccatttt tgctaaaagt aaaaaaaata tatatgaa atagaaaatt cgatcaaaat       600
aaaagtctca tttctctttc tgctttttta tgtttaccat cttgctggac taaaaaaaag    660
aagctttcga gtattccaca atgcatttttt atgttatgat tttagtggtt ttgacgaccc    720
tatcttatcc tatcttgatt accacaattc ccctgttcga caaaagttgc atttgtatac    780
aataatcgaa ttgtagcggg tatagtttag tggtaaaagt gtgattcgtt ctattatccc    840
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aaggtcactt agacattgaa aaattggatt attaaattgc gaaacataat    1020
ttttgaattg gatcaatact tccaattgaa taagtatgaa taaaggatcc atggatgaag    1080
atagaaagtt gatttctaat cgtaactaaa tcttcaattt cttatttgta agaagaaag     1140 tgaagcaaaa tagctattaa acgatgactt tggtttacta gagacatcaa catattgttt    1200
tagctcggtg gaaacaaaat ccttttcctc aggatcctat taaatagaaa tagagaacga    1260
aataactaga aaggttgtta gaatccccct cttctagaag gatcatctac aaagctattc    1320
gttttatctg tattcagatc aaaagctgac atagatgtta tgggtagaat tcttttttt     1380 tttctaattt tgttcacatc ttagatctat aaattgactc atctccataa aggagccgaa    1440
tgaaaccaaa gtttcatgtt cggttttgaa ttagagacgt tcaaaataat gaatcgacgt    1500
cgactataac ccctagcctt ccaagctaac gatgcgggtt cgattcccgc tacccgctct    1560
ctatctattt attctaaata ttttaatctt ttcattaaat caaatttagt ttattagtat    1620
tagtacatca ttgaatatac aattc                                          1645
```

<210> SEQ ID NO 26
<211> LENGTH: 1645
<212> TYPE: DNA
<213> ORGANISM: Damaye (L. barbarum Linn)

<400> SEQUENCE: 26

| | | | | | |
|---|---|---|---|---|---|
| ttaggatttg | gtctattcca | cacatttaac | taagaataag | aacaaaggat | ttcgaaaatt | 60 |
| gaaaaaaaaa | aatcaagtca | tcaacggaaa | gagagggatt | cgaaccctcg | gtacgattaa | 120 |
| ctcgtacaac | ggattagcaa | tccgccgctt | tagtccactc | agccatctct | cccaattgaa | 180 |
| aaagataatt | actacatgag | atagcacata | agataaagga | aagaatcttt | ctttctctct | 240 |
| tttcttcttt | actatattat | atagatatgt | acaacttta | tcatcaattt | cctttatctc | 300 |
| tttatctaaa | gtaaggaag | ggctcagaag | agccaagaat | atcaagaaaa | ataaagaaga | 360 |
| ccgcttttct | ttgtcttgat | tttgttcgaa | aggaccctct | tattctcatg | gcctggtctg | 420 |
| gtcagtaccc | agccgggcct | cttttgttcc | aacgaattg | aatttgaaaa | caaaaatgcc | 480 |
| tgttatagtt | gtaatatttc | attttaattg | aatagttaat | attcaagcaa | caagaaaaaa | 540 |
| ttcccatttt | tgctaaaagt | aaaaaaaata | tatatgaa | atagaaaatt | cgatcaaaat | 600 |
| aaaagtctca | tttctctttc | tgcttttta | tgtttaccat | cttgctggac | taaaaaaag | 660 |
| aagcttcga | gtattccaca | atgcattttt | atgttatgat | tttagtggtt | ttgacgaccc | 720 |
| tatcttatcc | tatcttgatt | accacaattc | ccctgttcga | caaagttgc | atttgtatac | 780 |
| aataatcgaa | ttgtagcggg | tatagtttag | tggtaaaagt | gtgattcgtt | ctattatccc | 840 |
| ttaaatagtt | aaagggtcct | tcggtttgat | tcgtattccg | atcaaaaact | ttatttctta | 900 |
| aaaggattaa | atccttttcc | tctcaatgac | agattcgaga | acaaatacac | attctcgtga | 960 |
| tttgtatcca | aaggtcactt | agacattgaa | aaattggatt | attaaattgc | gaaacataat | 1020 |
| ttttgaattg | gatcaatact | tccaattgaa | taagtatgaa | taaaggatcc | atggatgaag | 1080 |
| atagaaagtt | gatttctaat | cgtaactaaa | tcttcaattt | cttatttgta | aagaagaaag | 1140 |
| tgaagcaaaa | tagctattaa | acgatgactt | tggtttacta | gagacatcaa | catattgttt | 1200 |
| tagctcggtg | gaaacaaaat | cctttcctc | aggatcctat | taaatagaaa | tagagaacga | 1260 |
| aataactaga | aaggttgtta | gaatcccct | cttctagaag | gatcatctac | aaagctattc | 1320 |
| gttttatctg | tattcagatc | aaaagctgac | atagatgtta | tgggtagaat | tcttttttt | 1380 |
| tttctaattt | tgttcacatc | ttagatctat | aaattgactc | atctccataa | aggagccgaa | 1440 |
| tgaaaccaaa | gtttcatgtt | cggttttgaa | ttagagacgt | tcaaaataat | gaatcgacgt | 1500 |
| cgactataac | ccctagcctt | ccaagctaac | gatgcgggtt | cgattcccgc | tacccgctct | 1560 |
| ctatctattt | attctaaata | ttttaatctt | ttcattaaat | caaatttagt | ttattagtat | 1620 |
| tagtacatca | ttgaatatac | aattc | | | | 1645 |

<210> SEQ ID NO 27
<211> LENGTH: 1645
<212> TYPE: DNA
<213> ORGANISM: Baihua(L. barbarum)

<400> SEQUENCE: 27

| | | | | | |
|---|---|---|---|---|---|
| ttaggatttg | gtctattcca | cacatttaac | taagaataag | aacaaaggat | ttcgaaaatt | 60 |
| gaaaaaaaaa | aatcaagtca | tcaacggaaa | gagagggatt | cgaaccctcg | gtacgattaa | 120 |
| ctcgtacaac | ggattagcaa | tccgccgctt | tagtccactc | agccatctct | cccaattgaa | 180 |
| aaagataatt | actacatgag | atagcacata | agataaagga | aagaatcttt | ctttctctct | 240 |

```
tttcttcttt actatattat atagatatgt acaactttta tcatcaattt cctttatctc        300
tttatctaaa gtaaaggaag ggctcagaag agccaagaat atcaagaaaa ataaagaaga        360
ccgcttttct tgtcttgat tttgttcgaa aggaccctct tattctcatg gcctggtctg         420
gtcagtaccc agccgggcct cttttgttcc aacgaatttg aatttgaaaa caaaaatgcc        480
tgttatagtt gtaatatttc attttaattg aatagttaat attcaagcaa caagaaaaaa        540
ttcccatttt tgctaaaagt aaaaaaaata tatatatgaa atagaaaatt cgatcaaaat        600
aaaagtctca tttctctttc tgcttttttta tgtttaccat cttgctggac taaaaaaaag      660 aagcttcga gtattccaca atgcattttt atgttatgat tttagtggtt ttgacgaccc         720
tatcttatcc tatcttgatt accacaattc ccctgttcga caaaagttgc atttgtatac       780
aataatcgaa ttgtagcggg tatagtttag tggtaaaagt gtgattcgtt ctattatccc       840
ttaaatagtt aaagggtcct tcggtttgat tcgtattccg atcaaaaact ttatttctta      900
aaaggattaa atccttttcc tctcaatgac agattcgaga acaaatacac attctcgtga      960
tttgtatcca aaggtcactt agacattgaa aaattggatt attaaattgc gaaacataat     1020
ttttgaattg gatcaatact tccaattgaa taagtatgaa taaaggatcc atggatgaag     1080
atagaaagtt gatttctaat cgtaactaaa tcttcaattt cttatttgta aagaagaaag     1140
tgaagcaaaa tagctattaa acgatgactt tggtttacta gagacatcaa catattgttt     1200
tagctcggtg gaaacaaaat cctttcctc aggatcctat taaatagaaa tagagaacga     1260
aataactaga aaggttgtta gaatcccct cttctagaag gatcatctac aaagctattc     1320
gttttatctg tattcagatc aaaagctgac atagatgtta tgggtagaat tcttttttt     1380 tttctaattt tgttcacatc ttagatctat aaattgactc atctccataa aggagccgaa     1440
tgaaaccaaa gtttcatgtt cggttttgaa ttagagacgt tcaaaataat gaatcgacgt     1500
cgactataac ccctagcctt ccaagctaac gatgcgggtt cgattcccgc tacccgctct     1560
ctatctattt attctaaata ttttaatctt ttcattaaat caaatttagt ttattagtat     1620
tagtacatca ttgaatatac aattc                                            1645
```

<210> SEQ ID NO 28
<211> LENGTH: 1625
<212> TYPE: DNA
<213> ORGANISM: L. chinense Mill. var.

<400> SEQUENCE: 28

```
ttaggatttg gtctattcca cacatttaac taagaataag aacaaaggat ttcgaaaatt        60
gaaaaaaaaa tcaagtcatc aacggaaaga gagggattcg aaccctcggt acgattaact       120
cgtacaacgg attagcaatc cgccgcttta gtccactcag ccatctctcc caattgaata       180
aagataatta ctacatgaga tagcacataa gataaaggaa agaatctttc tttctctctt       240
ttcttctttc tatattatat agatatgtac aactttatc atcaatttcc tttatctctt       300
tatctaaagt aaaggaaggg ctcagaagag ccaagaatat caagaaaaat aaagaagacc       360
gcttttcttt gtcttgattt tgttcgaaag gaccctctta ttctcatggc ctggtctggt       420
cagtacccag ccgggcctct tttgttccaa cgaatttgaa acaaaaatg cctgttatag        480 ttgtaatatt tcattttaat tgaatagtta atattcaagc aacaagaaaa aattcccatt       540
tttgctaaaa gtaaaaaaaa aatatatata tgaaatagaa aattcgatca aaataaaagt      600
ctcatttctc tttctgcttt tttatgttta ccatcttgct ggactaaaaa aaagaagctt       660
```

```
tcgagtattc cacaatgcat ttttatgtta tgattttagt ggttttgacg accctatctt    720
atcctatctt gattaccaca attccctgt tcgacaaaag ttgcattgt atacaataat      780
cgaattgtag cgggtatagt ttagtggtaa aagtgtgatt cgttctatta tcccttaaat    840
agttaaaggg tccttcggtt tgattcgtat tccgatcaaa aactttattt cttaaaagga    900
tttaatcctt ttcctctcaa tgacagattc gagaacaaat acacattctc gtgatttgta    960
tccaaaggtc acttagacat tgaaaaattg gattatgaaa ttgcgaaaca taattttga   1020
attggatcaa tacttccaat tgaataagta tgaataaagg atccatggat gaagatagaa  1080
agttgatttc taatcgtaac taaatcttca atttcttatt tgtaaagaag aaagtgaagc  1140
aaaatagcta ttaaacgatg actttggttt actagagaca tcaacatatt gttttagctc  1200
ggtggaaaca aaatcctttt cctcaggatc ctattaaata gaaatagaga acgaaataac  1260
tagaaaggtt gttagaatcc ccctcttcta gaaggatcat ctacaaagct attcgtttta  1320
tctgtattca gaccaaaagc tgacatagat gttatgggta gaattctttt ttttttttcta 1380
attttgttca catcttagat ctataaattg actcatctcc ataaggagc cgaatgaaac   1440
caaagtttca tgttcggttt tgaattagag acgttcaaaa taatgaatcg acgtcgacta  1500
taaccccag ccttccaagc taacgatgcg ggttcgattc ccgctacccg ctctctatct   1560
atttattcta aatattttaa tcttttcatt aaatcaaatt tagtttatta gtattagtac  1620
atcat                                                              1625

<210> SEQ ID NO 29
<211> LENGTH: 1643
<212> TYPE: DNA
<213> ORGANISM: Lycium yunnanenseKuang et A.M.Lu

<400> SEQUENCE: 29
ttaggatttg gtctattcca cacatttaac taagaataag aacaaaggat ttcgaaaatt    60
gaaaaaaaaa tcaagtcatc aacggaaaga gagggattcg aaccctcggt acgattaact   120
cgtacaacgg attagcaatc cgccgcttta gtccactcag ccatctctcc caattgaaaa   180
agataattac tacatgagat agcacataag ataaaggaaa gaatcttct ttctctctttt  240
tcttctttct atattatata gatatgtaca acttttatca tcaatttcct ttatctcttt   300
atctaaagta aagaagggc tcagaagagc caagaatatc aagaaaaata aagaagaccg    360
cttttctttg tcttgatttt gttcgaaagg accctcttat tctcatggcc tggtctggtc   420
agtacccagc cgggcctctt ttgttccaac gaatttgaat ttgaaaacaa aaatgcctgt   480
tatagttgta atatttcatt ttaattgaat agttaatatt caagcaacaa gaaaaaattc   540
ccatttttgc taaaagtaaa aaaaaatat atatgaaata gaaaattcga tcaaaataaa   600
agtctcattt ctctttctgc tttttatgt ttaccatctt gctggactaa aaaaaagaag    660
ctttcgagta ttccacaatg cattttatg ttatgatttt agtggttttg acgaccctat    720
cttatcctat cttgattacc acaattcccc tgttcgacaa agttgcatt tgtatacaat    780
aatcgaattg tagcgggtat agtttagtgg taaaagtgtg attcgttcta ttatccctta   840
aatagttaaa gggtccttcg gtttgattcg tattccgatc aaaaacttta tttcttaaaa   900
ggatttaatc cttttcctct caatgacaga ttcgagaaca atacacatt ctcgtgattt   960
gtatccaaag gtcacttaga cattgaaaaa ttggattatg aaattgcgaa acataatttt  1020
tgaattggat caatacttcc aattgaataa gtatgaataa aggatccatg gatgaagata  1080
gaaagttgat ttctaatcgt aactaaatct tcaatttctt atttgtaaag aagaaagtga  1140
```

```
agcaaaatag ctattaaacg atgactttgg tttactagag acatcaacat attgttttag    1200
ctcggtggaa acaaatcct tttcctcagg atcctattaa atagaaatag agaacgaaat     1260
aactagaaag gttgttagaa tcccctctt ctagaaggat catctacaaa gctattcgtt     1320
ttatctgtat tcagaccaaa agctgacata gatgttatgg gtagaattct ttttttttt     1380 tctaattttg ttcacatctt agatctataa attgactcat ctccataaag gagccgaatg    1440
aaaccaaagt ttcatgttcg gttttgaatt agagacgttc aaaataatga atcgacgtcg    1500
actataaccc ctagccttcc aagctaacga tgcgggttcg attccgcta cccgctctct     1560 atctatttat tctaaatatt ttaatctttt cattaaatca aatttagttt attagtatta    1620
gtacatcatt gaatatacaa ttc                                            1643

<210> SEQ ID NO 30
<211> LENGTH: 1646
<212> TYPE: DNA
<213> ORGANISM: Manshenggouqi (L.bararum)

<400> SEQUENCE: 30
ttaggatttg gtctattcca cacatttaac taagaataag aacaaaggat ttcgaaaatt      60
gaaaaaaaaa aatcaagtca tcaacggaaa gagagggatt cgaaccctcg gtacgattaa    120
ctcgtacaac ggattagcaa tccgccgctt tagtccactc agccatctct cccaattgaa    180
aaagataatt actacatgag atagcacata agataaagga agaatctttt ctttctctct    240
tttcttcttt actatattat atagatatgt acaacttta tcatcaattt cctttatctc     300
tttatctaaa gtaaaggaag ggctcagaag agccaagaat atcaagaaaa ataaagaaga    360
ccgcttttct ttgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc attttaattg aatagttaat attcaagcaa caagaaaaaa    540
ttcccatttt tgctaaaagt aaaaaaaata tatatgaa atagaaaatt cgatcaaaat     600
aaaagtctca tttctctttc tgcttttta tgtttactat cttgctggac taaaaaaaag    660
aagctttcga gtattccaca atgcattttt atgttatgat tttagtggtt ttgacgaacc    720
tatcttatcc tatcttgatt accacaattc ccctgttcga caaaagttgc atttgtatac    780
aataatcgaa ttgtagcggg tatagtttag tggtaaagt gtgattcgtt ctattatccc     840
ttaaatagtt aaagggtcct tcggtttgat tcgtattccg atcaaaaact ttatttctta    900
aaaggattta atccttttcc tctcaatgac agattcgaga acaaatacac attctcgtga    960
tttgtatcca aaggtcactt agacattgaa aaattggatt attaaattgc gaaacataat   1020
ttttgaattg gatcaatact tccaattgaa taagtatgaa taaaggatcc atggatgaag   1080
atagaaagtt gatttctaat cgtaactaaa tcttcaattt cttatttgta agaagaaag    1140 tgaagcaaaa tagctattaa acgatgactt tggtttacta gagacatcaa catattgttt    1200
tagctcggtg gaaacaaaat ccttttcctc aggatcctat aaatagaaa tagagaacga    1260 aataactaga aaggttgtta gaatcccct cttctagaag gatcatctac aaagctattc    1320
gttttatctg tattcagacc aaaagctgac atagatgtta tgggtagaat tcttttttttt   1380 ttttataatt tgttcacat cttagatcta taaattgact catctccata aaggagccga   1440
atgaaaccaa agtttcatgt tcggttttga attagagacg ttcaaaataa tgaatcgacg   1500
tcgactataa cccctagcct tccaagctaa cgatgcgggt tcgattccg ctacccgctc   1560
```

```
tctatctatt tattcgaaat attttaatct tttcattaaa tcaaatttag tttattagta      1620
ttagtacatc attgaatata caattc                                          1646

<210> SEQ ID NO 31
<211> LENGTH: 1645
<212> TYPE: DNA
<213> ORGANISM: Ziguogouqi (L.barbarum)

<400> SEQUENCE: 31
ttaggatttg gtctattcca cacatttaac taagaataag aacaaaggat ttcgaaaatt        60
gaaaaaaaaa aatcaagtca tcaacggaaa gagagggatt cgaaccctcg gtacgattaa       120
ctcgtacaac ggattagcaa tccgccgctt tagtccactc agccatctct cccaattgaa       180
aaagataatt actacatgag atagcacata agataaagga aagaatcttt ctttctctct       240
tttcttcttt actatattat atagatatgt acaacttta tcatcaattt cctttatctc        300
tttatctaaa gtaaggaag ggctcagaag agccaagaat atcaagaaaa ataaagaaga        360
ccgcttttct ttgtcttgat tttgttcgaa aggaccctct tattctcatg gcctggtctg       420
gtcagtaccc agccgggcct cttttgttcc aacgaatttg aatttgaaaa caaaaatgcc       480
tgttatagtt gtaatatttc attttaattg aatagttaat attcaagcaa caagaaaaaa       540
ttcccatttt tgctaaaagt aaaaaaata tatatgaa atagaaaatt cgatcaaaat         600
aaaagtctca tttctctttc tgcttttta tgttaccat cttgctggac taaaaaaag         660 aagctttcga gtattccaca atgcatttt atgttatgat tttagtggtt ttgacgaccc       720
tatcttatcc tatcttgatt accacaattc ccctgttcga caaaagttgc atttgtatac      780
aataatcgaa ttgtagcggg tatagtttag tggtaaaagt gtgattcgtt ctattatccc      840
ttaaatagtt aaagggtcct tcggtttgat tcgtattccg atcaaaaact ttatttctta      900
aaaggattaa atccttttcc tctcaatgac agattcgaga acaaatacac attctcgtga      960
tttgtatcca aaggtcactt agacattgaa aaattggatt attaaattgc gaaacataat     1020
ttttgaattg gatcaatact tccaattgaa taagtatgaa taaggatcc atggatgaag     1080 atagaaagtt gatttctaat cgtaactaaa tcttcaattt cttatttgta aagaagaaag     1140
tgaagcaaaa tagctattaa acgatgactt tggtttacta gagacatcaa catattgttt     1200
tagctcggtg gaaacaaaat ccttttcctc aggatcctat taaatagaaa tagagaacga     1260
aataactaga aaggttgtta gaatccccct cttctagaag gatcatctac aaagctattc     1320
gttttatctg tattcagatc aaaagctgac atagatgtta tgggtagaat tcttttttt     1380 tttctaattt tgttcacatc ttagatctat aaattgactc atctccataa aggagccgaa     1440
tgaaaccaaa gttcatgtt cggttttgaa ttagagacgt tcaaaataat gaatcgacgt      1500
cgactataac ccctagcctt ccaagctaac gatgcgggtt cgattccgc tacccgctct     1560 ctatctattt attctaaata ttttaatctt ttcattaaat caaatttagt ttattagtat     1620
tagtacatca ttgaatatac aattc                                          1645

<210> SEQ ID NO 32
<211> LENGTH: 1664
<212> TYPE: DNA
<213> ORGANISM: Lycium dasystemum

<400> SEQUENCE: 32
ttaggatttg gtctattcca cacatttaac taagaataag aacaaaggat ttcgaaaatt        60
gaaaaaaaaa atcaagtcat caacggaaag agagggattc gaaccctcgg tacgattaac       120
```

```
tcgtacaacg gattagcaat ccgccgcttt agtccactca gccatctctc ccaattgaaa      180
aagataatta ctacatgaga tagcacataa gataaaggaa agaatctttc tttctctctt      240
ttcttcttta ctatattata tagatatgta caacttttat catcaatttc ctttatctct      300
ttatctaaag taaaggaagg gctcagaaga gccaagaata tcaagaaaaa taagaagac       360 cgcttttctt tgtcttgatt tgttcgaaa ggaccctctt attctcatgg cctggtctgg       420
tcagtaccca gccgggcctc ttttgttcca acgaatttga atttgaaaac aaaaatgcct      480
gttatagttg taatatttca ttttaatagt tgtaatattt cattttaatt gaatagttaa      540
tattcaagca acaagaaaaa attcccattt ttgctaaaag taaaaaaaat atatatatga      600
aatagaaaat tcgatcaaaa taaaagtctc atttctcttt ctgcttttt atgtttacca       660 tcttgctgga ctaaaaaaaa gaagctttcg agtattccac aacgcatttt tatgttatga      720
ttttagtggt tttgacgacc ctatcttatc ctatcttgat taccacaatt cccctgttcg      780 acaaagttg catttgtata caataatcga attgtagcgg gtatagttta gtggtaaaag       840
tgtgattcgt tctattatcc cttaaatagt taaagggtcc ttcggtttga ttcgtattcc      900
gatcaaaaac tttatttctt aaaggatta atccttttc ctctcaatga cagattcgag        960
aacaaataca cattctcgtg atttgtatcc aaaggtcact tagacattga aaaattggat     1020
tattaaattg cgaaacataa ttttgaatt ggatcaatac ttccaattga ataagtatga     1080
ataaaggatc catggatgaa gatagaaagt tgatttctaa tcgtaactaa atcttcaatt    1140
tcttatttgt aaagaagaaa gtgaagcaaa atagctatta aacgatgact ttggtttact    1200
agagacatca acatattgtt ttagctcggt ggaaacaaaa tccttttcct caggatccta    1260
ttaaatagaa atagagaacg aaataactag aaaggttgtt agaatccccc tcttctagaa    1320
ggatcatcta caaagctatt cgttttatct gtattcagac caaaagctga catagatgtt    1380
atgggtagaa ttcttttttt ttctaatttt gttcacatct tagatctata aattgactca   1440
tctccataaa ggagccgaat gaaaccaaag tttcatgttc ggttttgaat tagagacgtt   1500
caaaataatg aatcgacgtc gactataacc cctagccttc caagctaacg atgcgggttc   1560
gattcccgct acccgctctc tatctattta ttctaaatat tttaatcttt tcattaaatc   1620
aaatttagtt tattagtatt agtacatcat tgaatataca attc                     1664
```

<210> SEQ ID NO 33
<211> LENGTH: 1645
<212> TYPE: DNA
<213> ORGANISM: lycium

<400> SEQUENCE: 33

```
ttaggatttg gtctattcca cacatttaac taagaataag aacaaaggat ttcgaaaatt      60
gaaaaaaaaa atcaagtcat caacggaaag agagggattc gaaccctcgg tacgattaac    120
tcgtacaacg gattagcaat ccgccgcttt agtccactca gccatctctc ccaattgaaa    180
aagataatta ctacatgaga tagcacataa gataaaggaa agaatctttc tttctctcct    240
ttcttcttta ctatattata tagatatgta caacttttat catcaatttc ctttatctct    300
ttatctaaag taaaggaagg gctcagaaga gccaagaata tcaagaaaaa taagaagac     360 cgcttttctt tgtcttgatt tgttcgaaa ggaccctctt attctcatgg cctggtctgg     420
tcagtaccca gccgggcctc ttttgttcca acgaatttga atttgaaaac aaaaatgcct    480
gttatagttg taatatttca ttttaattga atagttaata ttcaagcaac aagaaaaaat    540
```

```
tcccattttt gctaaaagta aaaaaaatat atatatgaaa tagaaaattc gatcaaaata        600
aaagtctcat ttctctttct gcttttttat gttaccatc ttgctggact aaaaaaaaga         660
agctttcgag tattccacaa tgcattttta tgttatgatt ttagtggttt tgacgaccct        720
atcttatcct atcttgatta ccacaattcc cctgttcgac aaaagttgca tttgtataca       780
ataatcgaat tgtagcgggt atagtttagt ggtaaaagtg tgattcgttc tattatccct       840
taaatagtta aagggtcctt cggtttgatt cgtattccga tcaaaaactt tatttcttaa       900
aaggatttaa tccttttcct ctcaatgaca gattcgggaa caaatacaca ttctcgtgat      960
ttgtatccaa aggtcactta gacattgaaa aattggatta ttaaattgcg aaacataatt      1020
tttgaattgg atcaatactt ccaattgaat aagtatgaat aaaggatcca tggatgaaga      1080
tagaaagttg atttctaatc gtaactaaat cttcaatttc ttatttgtaa agaagaaagt      1140
gaagcaaaat agctattaaa cgatgacttt ggtttactag agacatcaac atattgtttt      1200
agctcggtgg aaacaaaatc cttttcctca ggatcctatt aaatagaaat agagaacgaa      1260
ataactagaa aggttgttag aatccccctc ttctagaagg atcatctaca aagctattcg      1320
ttttatctgt attcagacca aaagctgaca tagatgttat gggtagaatt ctttttttt       1380 tttctaattt tgttcacatc ttagatctat aaattgactc atctccataa aggagccgaa      1440
tgaaaccaaa gtttcatgtt cggttttgaa ttagagacgt tcaaaataat gaatcgacgt     1500
cgactataac ccctagcctt ccaagctaac gatgcgggtt cgattcccgc tacccgctct     1560
ctatctattt attctaaata ttttaatctt ttcattaaat caaatttagt ttattagtat     1620
tagtacatca ttgaatatac aattc                                            1645

<210> SEQ ID NO 34
<211> LENGTH: 1645
<212> TYPE: DNA
<213> ORGANISM: Xiaomaye (L. barbarum Linn)

<400> SEQUENCE: 34
ttaggatttg gtctattcca cacatttaac taagaataag aacaaaggat ttcgaaaatt       60
gaaaaaaaaa aatcaagtca tcaacggaaa gagagggatt cgaaccctcg gtacgattaa     120
ctcgtacaac ggattagcaa tccgccgctt tagtccactc agccatctct cccaattgaa     180
aaagataatt actacatgag atagcacata agataaagga aagaatcttt ctttctctct    240
tttcttcttt actatattat atagatatgt acaactttta tcatcaattt cctttatctc    300
tttatctaaa gtaaaggaag ggctcagaag agccaagaat atcaagaaaa ataaagaaga    360
ccgcttttct ttgtcttgat tttgttcgaa aggaccctct tattctcatg gcctggtctg    420
gtcagtaccc agccgggcct cttttgttcc aacgaatttg aatttgaaaa caaaaatgcc    480
tgttatagtt gtaatatttc attttaattg aatagttaat attcaagcaa caagaaaaaa   540
ttcccatttt tgctaaaagt aaaaaaaata tatatgaa atagaaaatt cgatcaaaat      600
aaaagtctca tttctctttc tgcttttta tgtttaccat cttgctggac taaaaaaaag   660
aagctttcga gtattccaca atgcattttt atgttatgat tttagtggtt tgacgaccc     720 tatcttatcc tatcttgatt accacaattc cctgttcga caaagttgc atttgtatac     780 aataatcgaa ttgtagcggg tatagtttag tggtaaaagt gtgattcgtt ctattatccc    840
ttaaatagtt aaagggtcct tcggtttgat tcgtattccg atcaaaaact ttatttctta    900
aaaggattaa atccttttcc tctcaatgac agattcgaga acaaatacac attctcgtga    960
tttgtatcca aggtcactt agacattgaa aaattggatt attaaattgc gaaacataat    1020
```

```
ttttgaattg gatcaatact tccaattgaa taagtatgaa taaaggatcc atggatgaag   1080
atagaaagtt gatttctaat cgtaactaaa tcttcaattt cttatttgta aagaagaaag   1140
tgaagcaaaa tagctattaa acgatgactt tggtttacta gagacatcaa catattgttt   1200
tagctcggtg gaaacaaaat ccttttcctc aggatcctat taaatagaaa tagagaacga   1260
aataactaga aaggttgtta gaatcccct cttctagaag gatcatctac aaagctattc    1320
gttttatctg tattcagatc aaaagctgac atagatgtta tgggtagaat tcttttttttt 1380
tttctaattt tgttcacatc ttagatctat aaattgactc atctccataa aggagccgaa   1440
tgaaaccaaa gtttcatgtt cggttttgaa ttagagacgt tcaaaataat gaatcgacgt   1500
cgactataac ccctagcctt ccaagctaac gatgcgggtt cgattcccgc tacccgctct   1560
ctatctattt attctaaata tttaatctt ttcattaaat caaatttagt ttattagtat    1620
tagtacatca ttgaatatac aattc                                         1645

<210> SEQ ID NO 35
<211> LENGTH: 1643
<212> TYPE: DNA
<213> ORGANISM: lycium

<400> SEQUENCE: 35
ttaggatttg gtctattcca cacatttaac taagaataag aacaaaggat ttcgaaaatt     60
gaaaaaaaaa atcaagtcat caacggaaag agagggattc gaaccctcgg tacgattaac   120
tcgtacaacg gattagcaat ccgccgcttt agtccactca gccatctctc ccaattgaaa   180
aagataatta ctacatgaga tagcacataa gataaaggaa agaatctttc tttctctctt   240
ttcttctttc tatattatat agatatgtac aacttttatc atcaatttcc tttatctctt   300
tatctaaagt aaaggaaggg ctcagaagag ccaagaatat caagaaaaat aaagaagacc   360
gcttttcttt gtcttgattt tgttcgaaag gaccctctta ttctcatggc ctggtctggt   420
cagtacccag ccgggcctct tttgttccaa cgaatttgaa tttgaaaaca aaaatgcctg   480
ttatagttgt aatatttcat attaattgaa tagttaatat tcaagcaaca agaaaaaatt   540
cccatttttg ctaaaagtaa aaaaaaaata tatatgaaat agaaaattcg atcaaaataa   600
aagtctcatt tctctttctg cttttttatg tttaccatct tgctggacta aaaaaaagaa   660
gctttcgagt attccacaat gcatttttat gttatgattt tagtggtttt gacgacccta   720
tcttatccta tcttgattac cacaattccc ctgttcgaca aaagttgcat ttgtatacaa   780
taatcgaatt gtagcgggta tagtttagtg gtaaaagtgt gattcgttct attatcccct   840
aaatagttaa agggtccttc ggtttgattc gtattccgat caaaaacttt atttcttaaa   900
aggatttaat cctttcctc tcaatgacag attcgagaac aaatacacat tctcgtgatt    960
tgtatccaaa ggtcacttag acattgaaaa attggattat gaaattgcga acataatttt  1020
ttcaattgga tcaatacttc caattgaata agtatgaata aaggatccat ggatgaagat  1080
agaaagttga tttctaatcg taactaaatc ttcaatttct tatttgtaaa gaagaaagtg  1140
aagcaaaata gctattaaac gatgactttg gtttactaga gacatcaaca tattgtttta  1200
gctcggtgga aacaaaatcc ttttcctcag gatcctatta aatagaaata gagaacgaaa  1260
taactagaaa ggttgttaga atccccctct tctagaagga tcatctacaa agctattcgt  1320
tttatctgta ttcagaccaa aagctgacat agatgttatg ggtagaattc tttttttttt  1380
tctaattttg ttcacatctt agatctataa attgactcat ctccataaag gagccgaatg  1440
```

```
aaaccaaagt tcatgttcg gttttgaatt agagacgttc aaaataatga atcgacgtcg    1500
actataaccc ctagccttcc aagctaacga tgcgggttcg attcccgcta cccgctctct    1560
aaatatttat tctaaatatt tagatctttt cattaaatca aatttagttt attagtatta    1620
gtacatcatt gaatatacaa ttc                                            1643

<210> SEQ ID NO 36
<211> LENGTH: 1644
<212> TYPE: DNA
<213> ORGANISM: Lycium dasystemumPojark

<400> SEQUENCE: 36
ttaggatttg gtctattcca cacatttaac taagaataag aacaaaggat ttcgaaaatt     60
gaaaaaaaaa atcaagtcat caacggaaag agagggattc gaaccctcgg tacgattaac    120
tcgtacaacg gattagcaat ccgccgcttt agtccactca gccatctctc ccaattgaaa    180
aagataatta ctacatgaga tagcacataa gataaaggaa agaatctttc tttctctctt    240
ttcttcttta ctatattata tagatatgta caactttat catcaatttc ctttatctct    300
ttatctaaag taaaggaagg gctcagaaga gccaagaata tcaagaaaaa taaagaagac    360
cgcttttctt tgtcttgatt ttgttcgaaa ggaccctctt attctcatgg cctggtctgg    420
tcagtaccca gccgggcctc ttttgttcca acgaatttga atttgaaaac aaaaatgcct    480
gttatagttg taatatttca ttttaattga atagttaata ttcaagcaac aagaaaaaat    540
tcccattttt gctaaagta aaaaatatat atatatgaaa tagaaaattc gatcaaaata    600
aaagtctcat ttctctttct gcttttttat gtttaccatc ttgctggact aaaaaaaaga    660
agctttcgag tattccacaa tgcattttta tgttatgatt ttagtggttt tgacgaccct    720
atcttatcct atcttgatta ccacaattcc cctgttcgac aaaagttgca tttgtataca    780
ataatcgaat tgtagcgggt atagtttagt ggtaaaagtg tgattcgttc tattatccct    840
taaatagtta aagggtcctt cggtttgatt cgtattccga tcaaaaactt tatttcttaa    900
aaggattaaa tccttttcct ctcaatgaca gattcgagaa caaatacaca ttctcgtgat    960
ttgtatccaa aggtcactta gacattgaaa aattggatta ttaaattgcg aaacataatt   1020
tttgaattgg atcaatactt ccaattgaat aagtatgaat aaaggatcca tggatgaaga   1080
tagaaagttg atttctaatc gtaactaaat cttcaatttc ttatttgtaa agaagaaagt   1140
gaagcaaaat agctattaaa cgatgacttt ggtttactag agacatcaac atattgtttt   1200
agctcggtgg aaacaaaatc ctttttcctca ggatcctatt aaatagaaat agagaacgaa   1260
ataactagaa aggttgttag aatccccctc ttctagaagg atcatctaca aagctattcg   1320
ttttatctgt attcagacca aaagctgaca tagatgttat gggtagaatt ctttttttt   1380 ttctaatttt gttcacatct tagatctata aattgactca tctccataaa ggagccgaat   1440
gaaaccaaag tttcatgttc ggttttgaat tagagacgtt caaaataatg aatcgacgtc   1500
gactataacc cctagccttc caagctaacg atgcgggttc gattcccgct acccgctctc   1560 tatctatta ttctaaatat tttaatctttt tcattaaatc aaatttagtt tattagtatt   1620
agtacatcat tgaatataca attc                                          1644

<210> SEQ ID NO 37
<211> LENGTH: 19
<212> TYPE: DNA
<213> ORGANISM: Artificial Sequence
<220> FEATURE:
<223> OTHER INFORMATION: The sequence is synthesized.
```

```
<400> SEQUENCE: 37
ttaggatttg gtctattcc                                                    19

<210> SEQ ID NO 38
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 38
gaattgtata ttcaatgatg                                                   20
```

DNA BARCODE FOR VARIETY IDENTIFICATION OF WOLFBERRY AND IDENTIFICATION METHOD THEREFOR

CROSS REFERENCE TO RELATED APPLICATION

The present application is based upon and claims priority to Chinese Application No. 2020106089828, filed on Jun. 30, 2020, and entitled "DNA barcode for species identification of *Lycium chinensis* and identification method therefor", and Chinese Application No. 2020103478862, filed on Apr. 28, 2020, and entitled "method for rapid identification of *Lycium chinensis* based on DNA barcode", the entire contents of which are incorporated herein by reference.

SEQUENCE LISTING

The present application contains a Sequence Listing which has been submitted in ASCII format via EFS-Web and is hereby incorporated by reference in its entirety. Said ASCII copy is named GBRSMJ043-POA_Sequence_Listing_20240709.txt, created Jul. 9, 2024, and is 82,317 bytes in size.

TECHNICAL FIELD

The present disclosure relates to the technical field of identification of Wolfberry species, especially relates to DNA barcodes for species identification of wolfberry and identification method therefor.

BACKGROUND

Wolfberry (*Lycium chinensis*) belongs to Lyciinae Wettst in Solaneae Reichb. of Solanaceae, it is a kind of plant, in particular to a deciduous shrub with perennial rootstock, whose fruit, root bark and leaves have high medicinal and health care value. There are 80 species of wolfberries, distributed all around the world. And in China, they are mainly distributed in Ningxia, Xinjiang, Gansu and Qinghai. Traditional morphological identification methods hardly work for species identification of *Lycium chinensis*, as they may have same origin or are close sib in one species, and they are similar in development morphology, the tissue structure and the chemical composition.

DNA barcoding (DNA barcode) can be used to recognize and identify target varieties using one or a few DNA fragments. It is characterized by simple operation, high accuracy, and rapid identification, etc. Presently, it has become a new research area and hotspot of interest in modern biological taxonomy. In recent years, researchers at home and abroad have carried out active exploration and studies on DNA barcode gene sequences suitable for plant identification.

A patent application CN110229927A with title "method for identifying wolfberry based on DNA barcoding and an application thereof", provides a method for identifying wolfberry based on DNA barcoding, wherein the gene sequence of a *Lycium ruthenicum* Murr. Identifyed DNA barcoding is LRITS2 (the sond internal transcribed spacer)/LrpsbA-trnH (a non-coding region between chloroplast genes psbA and trnH); the sequence LRITS2/LrpsbA-trnH of the *Lycium ruthenicum* Murr. Identified by DNA barcoding may be used together or one of them is used separately. The invention can efficiently and accurately distinguish the *Lycium ruthenicum* Murr. from other counterfeit products; it can be used for the identification in fruit powder, fruit shreds and others.

An article titled "Early Screening of intraspecies Hybrids of *Lycium barbarum* based on ITS barcode sequence", discloses early screening of intraspecies hybrid varieties of wolfberries by using a barcode sequence in ribosome internal transcribed spacer (ITS), wherein an improved cetyltrimethylammonium bromide (CTAB) method is used to extract DNA of wolfberry leaves, and a synthetic specific primers is used to amplify and clone the nrDNA ITS region, and then the target fragments are sequenced and analyzed. The results show, a group of Ningxia wolfberry including *L. barbarum* Linn (Ningqi 1 #), Ningqi 2 #and white-flowered wolfberry are used as parents for selective breeding and hybrid matching, and a cluster analysis of the hybrid offspring produced by the intraspecies crossbreeding based on the ITS barcode sequence to analyze the genetic relationship and differences between the hybrid offspring and their parents so as to conduct early screening of their hybrid offspring; as can be seen from the results, that the sequence based on ITS barcode can be used for early screening of hybrid progenies for breeding. However, the barcode database of wolfberries is deficient in both richness and number, and a lot of research is further needed.

SUMMARY OF THE INVENTION

The present disclosure provides DNA barcodes for species identification of Wolfberry (*Lycium chinensis*) and a method using them to identy *Lycium chinensis*, overcomes the problems in the prior art of delayed excavation and utilization of excellent wolfberry resources, unclear genetic background of species resources of wolfberries, unknown inter-species relationship, and deficiency in species richness and quantity in the barcode database of wolfberries. The present invention provides a method of quickly identifying molecular markers of wolfberries including *Lycium ruthenicum* Murr., Huangguo wolfberry, *Lycium barbarum* Yuanguo, *Lycium dasystemum*, local wolfberry species of Ningxia, the northern, Xinjiang, Yunnan and Hebei, and representative wolfberry species of different sources such as hybrid population, space mutation population and ploidy population on the basis of China's only *Lycium barbarum* germplasm resources nursery and the breeding materials obtained from the long-term development of new species of wolfberry, which can be applied to identification of wolfberry species.

The present invention provides a method of identifying *Lycium chinensis* species and distinguishing the interspecies relationship of *Lycium chinensis* by DNA barcoding. The invention also provides a trnG-trnS barcode database. The identification is completed by the following steps: aligning the trnG-trnS sequence of a sample to be identified with the sequence in the trnG-trnS barcode database, to identify the species of the wolfberry and determine the interspecies relationship of the wolfberry. This provides an effective basis for the species identification of wolfberry.

The technical solutions of the present invention are described as below.

For one purpose, the present disclosure provides a method for species identification of *Lycium chinensis* based on DNA barcode, the said DNA barcode is a trnG-trnS barcode.

The group of species to be identified includes: *L. barbarum* Linn (Ningqi 1 #), Ningqi 2 #, Ningqi 3 #, Ningqi 4 #, Ningqi 5 #, Ningqi 6 #, Ningqi 7 #and Ningnongqi 9 #, *L. barbarum* Linn. var. *auranticarpum* K. F. Ching var. nov., *Lycium barbarum* Bianguo, *Lycium ruthenicum* Murr., *L.*

*barbarum* Linn 5 #, *Lycium chinense* MilL. var. *potaninii* (Pojark.) A. M. Lu), Damaye (*L. barbarum* Linn), Baihua (*L. barbarum*),), *L. chinense* Mill. Va., *Lycium yunnanense* Kuang et A. M. Lu, Manshenggouqi (*L. barbarum*), Ziguogouqi (*L. barbarum*), *Lycium dasystemum*, Xiaomaye (*L. barbarum* Linn), *Lycium chinense, Lycium dasystemum* Pojark, Mengqi 1 #, Ningqicai 1 #, black half-bred wolfberry variant by space mutation, wolfberry variant by space mutation, *Lycium barbarum* Yuanguo, 9001 #wolfberry, *Lycium barbarum* Huangguo, Changji wolfberry, Hebei wolfberry and others.

Preferably, the said method for species identification of *Lycium chinensis* based on DNA barcoding, comprising the following steps:

1) Extracting a genomic DNA from a wolfberry sample;
2) Taking the said genomic DNA as a template, and using primers having nucleotide sequence of SEQ ID NO:37 and SEQ ID NO:38 to amplify sequence fragments of a trnG-tmS barcode to obtain a PCR amplified product;
3) Sequencing the said PCR amplified product;
4) Building a phylogenetic tree to identify the wolfberry.

The present disclosure provides a trnG-trnS DNA barcoding database consisting of SEQ ID NO:1-36.

The trnG-trnS DNA barcoding obtained by the present invention is used to build a phylogenetic tree, to perform homology ratio comparison to analyze and calculate base composition of the target sequence, the base variation frequency between sequences and the conversion frequency between sequences and their ratios, and the distribution difference of intra- and inter-species in sequences, thereby establishing a trnG-trnS DNA barcode identification technology system for identification of wolfberry species.

Preferably, in step 1), a DNA of the sample is extracted by a kit.

Preferably, in step 1), the kit is a DNA secure Plant Kit. Preferably, extraction of DNA using a kit has the following steps:

1.1 Extraction of DNA

Taking fresh and tender leaves of wolfberry plants as sample, washing up and stored at −80° C. Extracting total DNA using an extraction kit for new plant genomic DNA (DNA sure Plant Kit). The derailed extraction method is as follows:

1. 1. 1 Taking 100 g sample to a multifunctional high-efficiency biological sample preparation instrument and grind it for 2 minutes by 22 times/seconds; immediately adding 400 ul buffer solution LP1 and 6 ul RNase A (10 mg/ml)), oscillating it by a vortex method for 1 min, and staying it at a room temperature for 10 min.

1. 1. 2 Adding 130 ul buffer LP2, mixing well and oscillating by a vortex method for 1 min.

1. 1. 3 Centrifuging at 12000 rpm for 5 minutes, and transferring the supernatant to a new centrifugal tube.

1. 1. 4 Adding 1.5 times volume of buffer LP3 into the supernatant (checking if absolute ethanol is added before using), and fully oscillating the solution for 15 sec to mix it evenly; at this time, a flocculent precipitate may appear.

1. 1. 5 Adding the solution and flocculent precipitate obtained in the previous step into an adsorption column CB3 (which is placed in a collection tube), centrifuging the mixture at 12000 rpm for 30 s, discarding the waste fluid, and putting the adsorption column CB3 into the collection tube.

1. 1. 6 Adding 600 ul rinse solution PW to the adsorption column CB3 (checking if the absolute ethanol is added before using), centrifuging the solution at 12000 rpm for 30 s, discarding the waste fluid, and putting the adsorption column CB3 into the collection tube. (Note: If the adsorption column membrane is green, adding 500 ul absolute ethanol to the adsorption column CB3, centrifuging at 12000 rpm for 30 s, discarding the waste fluid, and putting the adsorption column CB3 into the collection tube)

1. 1. 7 Repeating the step 1.1.6.

1. 1. 8 Putting the adsorption column CB3 into the collection tube, centrifuging at 12000 rpm for 2 minutes, and discarding the waste fluid; placing the adsorption column CB3 at a room temperature for 15 minutes to remove the remaining rinse solution in the adsorption material thoroughly.

1. 1. 9 Transferring the adsorption column CB3 into a clean centrifugal tube, and dropping 100 ul elution buffer TE in the air into the middle of the adsorption membrane, staying at room temperature for 2 minutes, centrifuging at 12000 rpm for 2 minutes, and collecting the solution into the centrifugal tube.

1. 1. 10 Repeating the step 1.19. Keeping the DNA product at −80° C. to prevent DNA degradation.

1.2 DNA Concentration and Purity Detection 1. 2. 1 Agarose Gel Electrophoresis Detection Preparing 1.2% agarose gel with 1.2 g agarose and 100 ml 1*TAE buffer, adding a detection system of 4 ul ddH$_2$O+1 ul DNA sample (undiluted)+1 ul 6*loading buffer into a PCR tube for agarose gel electrophoresis, and observing the test results under a UV gel imaging system.

1. 2. 2 UV Spectrophotometer Detection

Preheating a UV spectrophotometer, and adding 99 ul ddH$_2$O+1 ul DNA sample (undiluted) into the PCR tube for detection. The test results show the sample concentration and OD$_{260}$/OD$_{280}$ ratio, OD$_{260}$/OD$_{280}$ ratio should be within 1.7-1.9, if an elution buffer is not used in eluting, but ddH$_2$O is used, the ratio will be lower, because the PH value and the presence of ions could affect the light absorption value, but it does not mean that the purity is low.

Preferably, in the above step 2), the PCR amplification reaction system includes: 2.1 pre-denaturation at 94° C. for 2 min; 2.2 denaturation at 94° C. for 30 s, annealing at 55° C. for 30 s (annealing temperature is adjustable within 58-60° C.), extension at 72° C. for 2 min, with 35 cycles: 2.3 incubation at 72° C. for 10 min; 2.4 storage at 4° C. After the PCR product is subjected to 1.0% agarose gel electrophoresis, observing the amplification result under a UV gel imaging system.

Preferably, in the above step 3), the sequencing is performed by the following steps:

3.1 PCR Product Cloning:

Taking a AxyPrep DNA gel extraction kit to recover a target band, and taking 1.2% agarose gel electrophoresis to perform recovery detection, and taking the purified target DNA as a sequencing template; use a pLB zero background fast cloning kit (Lethal Based Simple Fast Cloning Kit) to attach the recovered product to a T vector (pGEM-T) and then transfer it to a *Escherichia coli* DH5 α for culturing; screen the positive colonies by Blue-White Screening and conduct PCR detection for the colonies. Observing amplification results under a UV gel imaging system.

3.2 Sequence Sequencing and Analysis:

Performing sequencing of the DNA sequences of positive clones, and performing homology alignment with the sequences published in NCBI to analyze the sequences. Refer to specific operations below:

In the present invention, after PCR detection of positive bacterial colonies, the colonies containing target fragments are cultured in a LB fluid medium, and 3 colonies of each group are taken and sent to perform Sanger sequencing, thus to obtain the trnG-trnS sequence.

A homology alignment is made by Use DNAMAN on the DNA barcoding gene sequences obtained and the sequences published in NCBI database, and the DNA barcoding gene sequences of wolfberries are aligned by a Clustal X program, phylogenetic analysis software MEGA7.0 is applied to calculate the base composition of the target sequence, the base variation frequency between sequences and the conversion frequency between sequences and their ratios, the distribution difference of intra- and inter-species in sequences is compared to build a phylogenetic tree, thereby establishing a trnG-trnS DNA barcode identification technology system for identification of wolfberry species.

Another purpose of the present invention is to provide a trnG-trnS barcode database for wolfberry samples established according to the above methods, comprising 36 groups of trnG-trnS barcode, indicated by nucleotide sequence SEQ ID NO:1-36.

Another purpose of the present invention is to provide an application of the trnG-trnS barcode database for wolfberry samples in identification of wolfberry species.

Preferably, based on the application of the trnG-trnS barcode database for wolfberry samples in identification of a wolfberry species, the steps are given as below: Aligning the trnG-trnS sequence of a sample to be identified with the sequence in the trnG-trnS barcode database, and then performing species identification of the sample.

Aligning the trnG-trnS sequence of a sample to be identified with the sequence in the trnG-trnS barcode database, effectively identify the species of the wolfberry and determine the interspecies relationship of the wolfberry, and further determine the interspecies relationship between the wolfberry to be identified and the wolfberry in the barcoding database, thereby providing an effective basis for classification and identification of wolfberry species.

Preferably, the trnG-trnS sequence of the sample to be identified is also obtained by the steps of genomic DNA extraction, PCR amplification and sequencing of PCR amplification products. The operation steps are the same as those in steps 1), 2) and 3) described in above.

The present invention has the following advantages compared to the prior art:

(1) An identification method of wolfberry species is established based on a trnG-trnS barcode gene for the first time, and it can be applied for identification of *L. barbarum* Linn, *L. barbarum* Linn. var. *auranticarpum* K. F. Ching var. nov., *Lycium ruthenicum* Murr., *Lycium chinense* Mill. var. *potaninii* (Pojark.) A. M. Lu, Damaye (*L. barbarum* Linn), *L. chinense* Mill. Var., *Lycium yunnanense* Kuang et A. M. Lu, Manshenggouqi (*L. barbarum*) Ziguogouqi (*L. barbarum*), *Lycium dasystemum* and other species.

(2) The DNA barcode provided by the present invention can be applied to building a wolfberry phylogenetic tree to be used for studying intra-species and inter-species phylogeny of wolfberries, and it reveals the genetic diversity and relationship of wolfberries based on trnG-trnS genes, thereby providing an effective basis for identification, classification and phylogenetic study of wolfberry species;

(3) Accurate identification of wolfberry species based on trnG-trnS gene.

(4) A trnG-tmS barcode database is provided, which can be used to rapidly identity wolfberry species. The group of wolfberry species comprises Ningxia, the northern, Xinjiang, Yunnan, Hebei and Sichuan, and representative wolfberry species of different sources, such as hybrid population, space mutation population and ploidy population, such as *Lycium ruthenicum* Murr., Huangguo wolfberry, *Lycium barbarum* Yuanguo, *Lycium dasystemum*, which are all known as China's representative species, hence, it provides an effective bases for classification and identification of wolfberry species.

Align the trnG-trnS sequence of a sample to be identified with the sequence in the trnG-trnS barcode database, effectively identify the species of the wolfberry and determine the interspecies relationship of the wolfberry, thereby providing an effective basis for classification and identification of wolfberry species.

DETAILED DESCRIPTION

Figure 1:
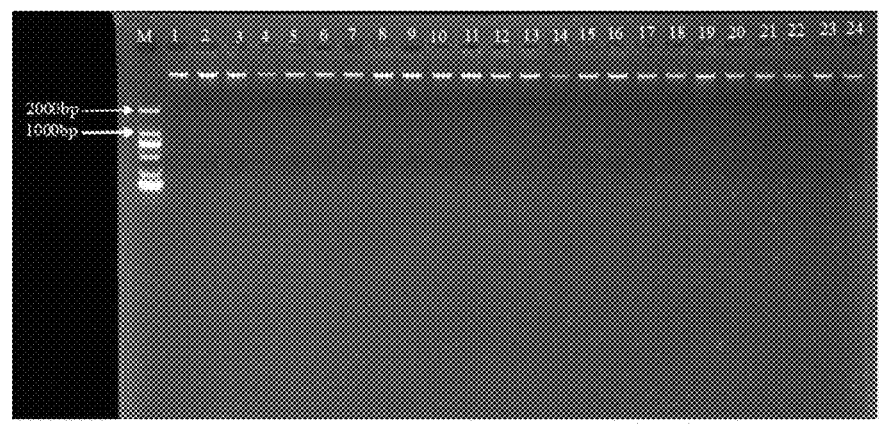
FIG. 1 shows a DNA extraction and detection result of a wolfberry sample of Embodiment 1 described in the present embodiment, wherein lane M: Marker (DL2000 DNA molecular marker), and FIG. (a) shows the DNA extraction and detection result of No. 1-24 wolfberry species of Embodiment 1; FIG. (b) shows the DNA extraction and detection results of No. 25-36 wolfberry species in Embodiment 1.

The present invention is described in details below by referencing specific embodiments, unless otherwise stated, the technical means used in the present invention are methods known to those skilled in the art, and the embodiments are understood as illustrative without limiting the scope of the invention. The scope of the present invention are defined only by the Claims. For those skilled in the art, any change or alteration of the material composition and dosage in these embodiments shall also fall within the scope of protection of the invention as long as it does not deviates from the nature and scope of the invention. As below, the present invention is further explained in combination with the following specific embodiments.

Embodiment 1 Identification of Wolfberry Samples and Construction of trnG-trnS Barcode Database The following gives detailed description of the solutions of the present invention in combination with specific embodiments.

1. trnG-trnS Barcode Database of Wolfberry Samples

A total of 36 wolfberry samples with partial similar morphology from different regions are collected, the trnG-trnS barcode database of wolfberry samples is constructed. See Table 1 for details:

TABLE 1

Wolfberry samples (trnG-trnS barcode database of wolfberry samples)

| No. | Latin name | Species Name | Designation | Type of resource | SEQ ID NO: |
|---|---|---|---|---|---|
| 1 | Ningqi No. 1 (*L. barbarum* Linn) | *L. barbarum* Linn(Ningqi 1#) | Ningqi1 | Bred varieties | 1 |
| 2 | Ningqi No.2 (*L. barbarum* Linn) | Ningqi 2# | Ningqi2 | Bred varieties | 2 |
| 3 | Ningqi No.3 (*L. barbarum* Linn) | Ningqi 3# | Ningqi3 | Bred varieties | 3 |
| 4 | Ningqi No.4 (*L. barbarum* Linn) | Ningqi 4# | Ningqi4 | Bred varieties | 4 |
| 5 | Ningqi No.5 (*L. barbarum* Linn) | Ningqi 5# | Ningqi5 | Bred varieties | 5 |
| 6 | Ningqi No.6 (*L. barbarum* Linn) | Ningqi 6# | Ningqi6 | Bred varieties | 6 |
| 7 | Ningqi No.7 (*L. barbarum* Linn) | Ningqi 7# | Ningqi7 | Bred varieties | 7 |
| 8 | *L. barbarum* Linn | Ningnongqi 9# | Ningnongqi9 | Bred varieties | 8 |
| 9 | *L. barbarum* Linn. var. auranticarpum K. F. Ching var. nov. | *L. barbarum* Linn. var. auranticarpum K. F. Ching var. nov. | Huangguobian | Bred varieties | 9 |
| 10 | Mengqi 1 (*L. barbarum*) Source: Published literature 5 | Mengqi 1# | Mengqi1 | Bred varieties | 10 |
| 11 | *Lycium barbarum* Bianguo | *Lycium barbarum* Bianguo | Bianguo | Bred varieties | 11 |
| 12 | *Lycium ruthenicum* Murr. | *Lycium ruthenicum* Murr. | Heiguo | Bred varieties | 12 |
| 13 | Source: Published literature 2 | Ningqicai 1# | Ningqicai1 | Bred varieties | 13 |
| 14 | *L. barbarum* Linn | Ningnongqi 5# | W-12-30 | Wolfberry variant by space mutation | 14 |
| 15 | Source: Published literature 1 | HZ-13-01 | HZ-13-01 | Black half-bred wolfberry variant by space mutation, | 15 |
| 16 | Source: Published literature 1 | ZH-13-08 | ZH-13-08 | Wolfberry variant by space mutation | 16 |
| 17 | Source: Published literature 1 | W-12-27 | W-12-27 | Black half-bred wolfberry variant by space mutation, | 17 |
| 18 | Source: Published literature 1 | W-11-15 | W-11-15 | Black half-bred wolfberry variant by space mutation, | 18 |
| 19 | Source: Published literature 1 | W-13-26 | W-13-26 | Black half-bred wolfberry variant by space mutation, | 19 |
| 20 | Source: Published literature 1 | W-12-26 | W-12-26 | Black half-bred wolfberry variant by space mutation, | 20 |
| 21 | *Lycium chinense* MilL. var. potaninii (Pojark.) A. M. Lu | Lycium chinense MilL. var. potaninii (Pojark.) A. M. Lu | Beifang | Imported varieties | 21 |
| 22 | Source: Published literature 1 | *Lycium barbarum* Yuanguo | Yuanguo | Bred varieties | 22 |
| 23 | Source: Published literature 4 | 9001 | 9001 | Bred varieties | 23 |
| 24 | Source: Published literature 3 | *Lycium barbarum* Huangguo | Huangguo | Bred varieties | 24 |
| 25 | *Lycium chinense* See notes for published information | *Lycium chinense* | Sichuan | Imported varieties | 25 |

TABLE 1-continued

Wolfberry samples (trnG-trnS barcode database of wolfberry samples)

| No. | Latin name | Species Name | Designation | Type of resource | SEQ ID NO: |
|---|---|---|---|---|---|
| 26 | Damaye (*L. barbarum* Linn) | Damaye (*L. barbarum* Linn) | Damaye | Bred varieties | 26 |
| 27 | Baihua(*L. barbarum*) | Baihua (*L. barbarum*) | Baihua | Imported varieties | 27 |
| 28 | *L. chinense* Mill. var. | *L. Chinense* Mill. var. | Zhongguo | Imported varieties | 28 |
| 29 | *Lycium* yunnanenseKuang et A. M. Lu | *Lycium* yunnanenseKuang et A. M. Lu | Yunnan | Imported varieties | 29 |
| 30 | Manshenggouqi (*L.bararum*) | Manshenggouqi (*L.barbarum*) | Mansheng | Imported varieties | 30 |
| 31 | Ziguogouqi (*L.barbarum*) | Ziguogouqi (*L.barbarum*) | Zibing | Imported varieties | 31 |
| 32 | *Lycium dasystemum* | *Lycium dasystemum* | Hongzhi | Imported varieties | 32 |
| 33 | Source: Published literature 1 | Hebei wolfberry | Hebei | Imported varieties | 33 |
| 34 | Xiaomaye (*L. barbarum* Linn) | Xiaomaye (*L. barbarum* Linn) | Xiaomaye | Bred varieties | 34 |
| 35 | Source: Published literature 1 | Changji wolfberry | Changji | Imported varieties | 35 |
| 36 | *Lycium* dasystemumPojark | *Lycium* dasystemumPojark | Xinjiang | Imported varieties | 36 |

(Note:
Species No. 15-20, 22, 33, 35 are from published literature 1: Identification of 21 wolfberry plants based on psbA-trnH sequence barcode [J] by "Wan Ru, Wang Yajun, An Wei, et al. A species disclosed in Jiangsu Agricultural Sciences, 2019, 47(01):64-67"; species no. 13 is from the published literature 2: A New Method of Identification on Edible Lycium Linn. Germplasm Resource—nrDNA ITS Sequencing [J] by "Shi Zhigang, An Wei, Jiao Enning, et al". Agricultural Science & Technology (2):64-65+111." Table 1; species no.24 is from the published literature 3:" Genetic Polymorphism of Eighteen Lycium barbarum Resources Based on nrDNA ITS Sequence [J] by Shi Zhigang; Anhui Agricultural Science (24): 10379-10380. "Table 1; species no.23 is from the published literature 4: Genetic Polymorphism of Eighteen *Lycium barbarum* Resources Based on nrDNA ITS Sequence [J] by Shi Zhigang; Anhui Agricultural Science (24):10379-10380. Table 1; species no.10 is from the published literature 5: SSR information analysis and molecular marker development of the transcription group of *Lycium barbarum*. [J] by Yin Yue, An Wei, Zhao Jianhua, et al. Journal of Zhejiang A&F University, 2019, 36(02):215-221."; No. 25, Resource No.: 1111C0003121000044, classification code: 11132115107, source: Baidu Baike)

2. Identification of Wolfberry Samples and Construction Method of trnG-trnS Barcode Database 1) Extraction of DNA Collecting 36 samples of fresh and tender leaves of the said 36 wolfberry plants from the base of Wolfberry Engineering Technology Institute, Ningxia Academy of Agriculture and Forestry Sciences, putting them in a 5 ml cryogenic tube separately, make a mark on the tubes and add liquid nitrogen to store the sample at −80° C. Sampling time: June 2018, place of sampling: Wolfberry National Forest Tree Germplasm Resources Repository in Yinchuan City, Ningxia. See Table 1 for sample details.

Extract the total DNA using an extraction kit for new plant genomic DNA (DNA sure Plant Kit), and following the extraction method as follows:

(1) Taking 100 g sample to a multifunctional high-efficiency biological sample preparation instrument and grind it for 2 minutes (22 times/s); immediately adding 400 ul buffer solution LP1 and 6 ul RNase A (10 mg/ml), oscillating it by a vortex method for 1 min, and staying it at a room temperature for 10 min.

(2) Adding 130 ul buffer LP2, mixing it well and oscillating it by a vortex method for 1 min.

(3) Centrifuging it at 12000 rpm for 5 minutes, and transferring the supernatant to a new centrifugal tube.

(4) Adding 1.5× volume buffer LP3 (please check if absolute ethanol is added before using), and fully oscillating the solution to mix it evenly for 15 s; at this time, a flocculent precipitate may appear.

(5) Adding the solution and flocculent precipitate obtained in the previous step into an adsorption column CB3 (which is placed in a collection tube), centrifuging the mixture at 12000 rpm for 30 s, discarding the waste fluid, and putting the adsorption column CB3 into the collection tube.

(6) Adding 600 ul rinse solution PW to the adsorption column CB3 (please check if the absolute ethanol is added before using), centrifuging the solution at 12,000 rpm for 30 s, discarding the waste fluid, and putting the adsorption column CB3 into the collection tube. (Note: If the adsorption column membrane is green, add 500 ul absolute ethanol to the adsorption column CB3, centrifuge it at 12,000 rpm for 30 s, discard the waste fluid, and put the adsorption column CB3 into the collection tube)

(7) Repeating step 6.

(8) Putting the adsorption column CB3 back to the collection tube, centrifuging at 12,000 rpm for 2 minutes, and discarding the waste fluid; putting the adsorption column CB3 at a room temperature for 15 minutes to dry the remaining rinse solution in the adsorption material thoroughly.

(9) Transferring the adsorption column CB3 into a clean centrifugal tube, and dropping 100 ul elution buffer TE into the middle of the adsorption membrane, staying it at room temperature for 2 minutes, centrifuging at 12,000 rpm for 2 minutes, and collecting the solution into the centrifugal tube.

(10) Repeating step 9. Store the DNA product at −80° C. to prevent DNA degradation.

2) DNA Concentration and Purity Detection

① Agarose Gel Electrophoresis Detection

Preparing 1.2% agarose gel with 1.2 g agarose and 100 ml 1*TAE buffer, adding a detection system of 4 ul ddH$_2$O+1 ul DNA sample (undiluted)+1 ul 6*loading buffer into a PCR tube for agarose Gel electrophoresis, and observing the test results under a UV gel imaging system, as shown in FIG. 1.

② UV Spectrophotometer Detection

Preheating a UV spectrophotometer, and adding 99 ul ddH$_2$O+1 ul DNA sample (undiluted) into the PCR tube for detection. The test results show the sample concentration and OD$_{260}$/OD$_{280}$ ratio, OD$_{260}$/OD$_{280}$ should be 1.7-1.9; if an elution buffer is not used in eluting, but ddH$_2$O is used, the ratio will be lower, because the pH value and the presence of ions could affect the light absorption value, but it does not mean that the purity is low.

3) PCR Amplification

Taking the DNA obtained in step 1) as a template, adding a reagent required for amplification such as a primer for PCR amplification. The specific primer and amplification system are shown in Table 2 and Table 3.

(1) The Design Primers are as Follows:

TABLE 2

Universal primer of trnG-trnS barcode genes

| Name of primer | SEQ ID NO: | SEQ ID NO: of primer (5' to 3') |
|---|---|---|
| trnGS-F | 37 | TTAGGATTTGGTCTATTCC |
| trnGS-R | 38 | GAATTGTATATTCAATGATG |

2) PCR Amplification System:

Conduct PCR amplification for the genomic DNA of the test material using the above primers. The amplification system is shown in Table 3:

TABLE 3

DNA barcoding reaction system

| Amplification system | 50 ul system |
|---|---|
| PCR-Grade Water | 15.0 μl |
| 2X Ex taq Buffer (takara) | 25.0 μl |
| dNTP Mix (10 mM) | 1.0 μl |
| Ex taq (takara) | 1.0 μl |
| DNA | 5.0 μl |
| primer F (10X) | 1.5 μl |
| primer R (10X) | 1.5 μl |

Figure 2:
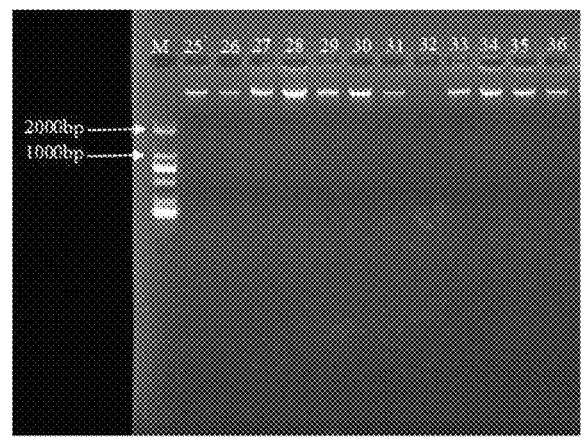
FIG. 2 shows a trnG-trnS sequence PCR amplification result of part of wolfberry samples in embodiment 1, wherein lane M: Marker (DL2000 DNA molecular marker) and lanes 1-4 represent No. 26 Damaye PCR product in Embodiment 1; lanes 1-4 are for PCR validation of the samples repeated for four times.

The PCR reaction includes: 1) pre-denaturation at 94° C. for 2 min; 2) denaturation at 94° C. for 30 s, annealing at 55° C. for 30 s (annealing temperature is adjustable between 58-60° C.), extension at 72° C. for 2 min, with 35 cycles; 3) incubation at 72° C. for 10 min; 4) storage at 4° C. After the PCR product is subjected to 1.0% agarose gel electrophoresis, observing the amplification result under a UV gel imaging system (FIG. 2). The amplification result shows the trnG-tmS sequence.

Figure 3:
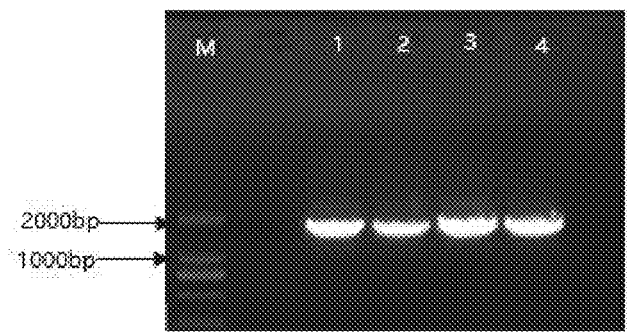
FIG. 3 shows a detection diagram of trnG-trnS sequence cloning results of No. 26 Damaye wolfberry samples in Embodiment 1, wherein M: Marker (DL2000 DNA molecular marker), lane 1: positive cloning; lane 2: negative clone; lanes 3-9: positive clones (multiple replicates).

4) PCR Product Cloning:

Use a AxyPrep DNA gel recovery kit to recover a target band, and use 1.2% agarose gel electrophoresis for recovery detection, and take the purified target DNA as a sequencing template; use a pLB zero background fast cloning kit to attach the recovered product to a T vector (pGEM-T) and then transfer it to a Escherichia coli DH5 α for culturing; note to observe the amplification result under a UV gel imaging system (FIG. 3); with No. 26 Damaye (L. barbarum Linn) as an example, as shown in FIG. 3, according to the analysis FIG. 3, the trNg-TRNS genes have good amplification results with clear bands and obvious cloning effect.

5) Sequence Sequencing and Analysis

In the present invention, after PCR detection of positive bacterial colonies, the colonies containing target fragments are cultured in a LB fluid medium, and 3 colonies of each material are taken and sent to Sangon Biotech (Shanghai) Co., Ltd. for sequencing, thus to obtain the tRNG-trnS sequences of 36 samples.

The DNA barcode gene sequences obtained are aligned with the sequence published in the NCBI database by DNAMAN, and the DNA barcode gene sequences of 36 wolfberry samples are aligned using a Clustal X program; with the help of phylogenetic analysis software MEGA7.0, the relevant data of the trnG-trnG sequence are obtained as below: the total length is 1673 bp, there are 1617 conservative sites, accounting for 96.6%; 30 variant sites, accounting for 1.8%, including 10 information sites and 20 descendant sites; and the base conversion value is 0.7, and the average GC content accounts for 32.3%.

After sequence alignment and analysis, the result indicates, 10 germplasms of L. barbarum Linn. var. auranticarpum K. F. Ching var. nov., Lycium ruthenicum Murr., L. barbarum Linn, HZ-13-01, ZH-13-08, W-12-27, W-11-15, W-13-26, W-12-26, Changji wolfberry has a base A missing at 256 bp; has a transversion at 526 bp, 592 bp, 1029 bp; a conversion at 1365 bp; a conversion from CT to AA at 1592 bp; a conversion from TA to AG at 1612 bp; wherein, germplasms of L. barbarum Linn. var. auranticarpum K. F. Ching var. nov., Lycium ruthenicum Murr. and Changji wolfberry are transposed at 935 bp; L. barbarum Linn. var. auranticarpum K. F. Ching var. nov. has 2 base TTs inserted at 1410 bp; Lycium ruthenicum Murr. has a base T inserted at 1410 bp; Changji wolfberry has 1 base A missing at 72 bp, and a transversion at 1051 bp, and the remaining 7 germplasms are converted at 1074 bp; HZ-13-01 has a conversion at 1062 bp; W-12-27 has a conversion at 1582 bp; W-13-26 bp has 1 base A missing at 529 bp and a conversion at 1093 bp; W-12-26 has a conversion at 1036 bp and has a base T missing at 1409 bp.

Ningqi 4, Lycium chinense MilL. var. potaninii (Pojark.) A. M. Lu, Lycium barbarum Yuanguo, Lycium dasystemum, Hebei wolfberry and Lycium dasystemum Pojark have a base A missing at 72 bp; are converted at 1365 bp; wherein L. barbarum Linn 4 is inserted with 2 bases TT at 1410 bp; Lycium chinense MilL. var. potaninii (Pojark.) A. M. Lu has a conversion at 55 bp and a transversion at 935 bp; Lycium dasystemum has a conversion at 423, 708 bp, and have 1 base T missing at 1409 bp, a 22 bp sequence (i.e. CAT-TIAATAGTTGTAATATTT) inserted at 501 bp; Hebei wolfberry has a conversion at 241 bp and 964 bp, and a transversion at 935 bp.

L. chinense Mill. var. and Lycium yunnanense Kuang et A. M. Lu have 2 base AA missing at 72 bp; 1 base A missing at 252 bp; have a transversion at 935 bp and 1029 bp; L. chinense Mill. Var. has a base T inserted at 181 bp; has 6 bp sequence (i.e. TTTGAA) at 464 bp, and has 3 base AAA inserted at 592 bp; Lycium yunnanense Kuang et A. M. Lu has a conversion at 381 bp and a transversion at 592 bp.

L. barbarum Linn 2 has a conversion at 1471 bp, Lycium barbarum Huangguo has a conversion at 1097 bp and 1252 bp; Manshenggouqi (L. barbarum) has a conversion at 664 bp, 935 bp and 1365 bp; and a base T inserted at 1410 bp; and has a transversion at 744 bp and 1603 bp.

Figure 4:
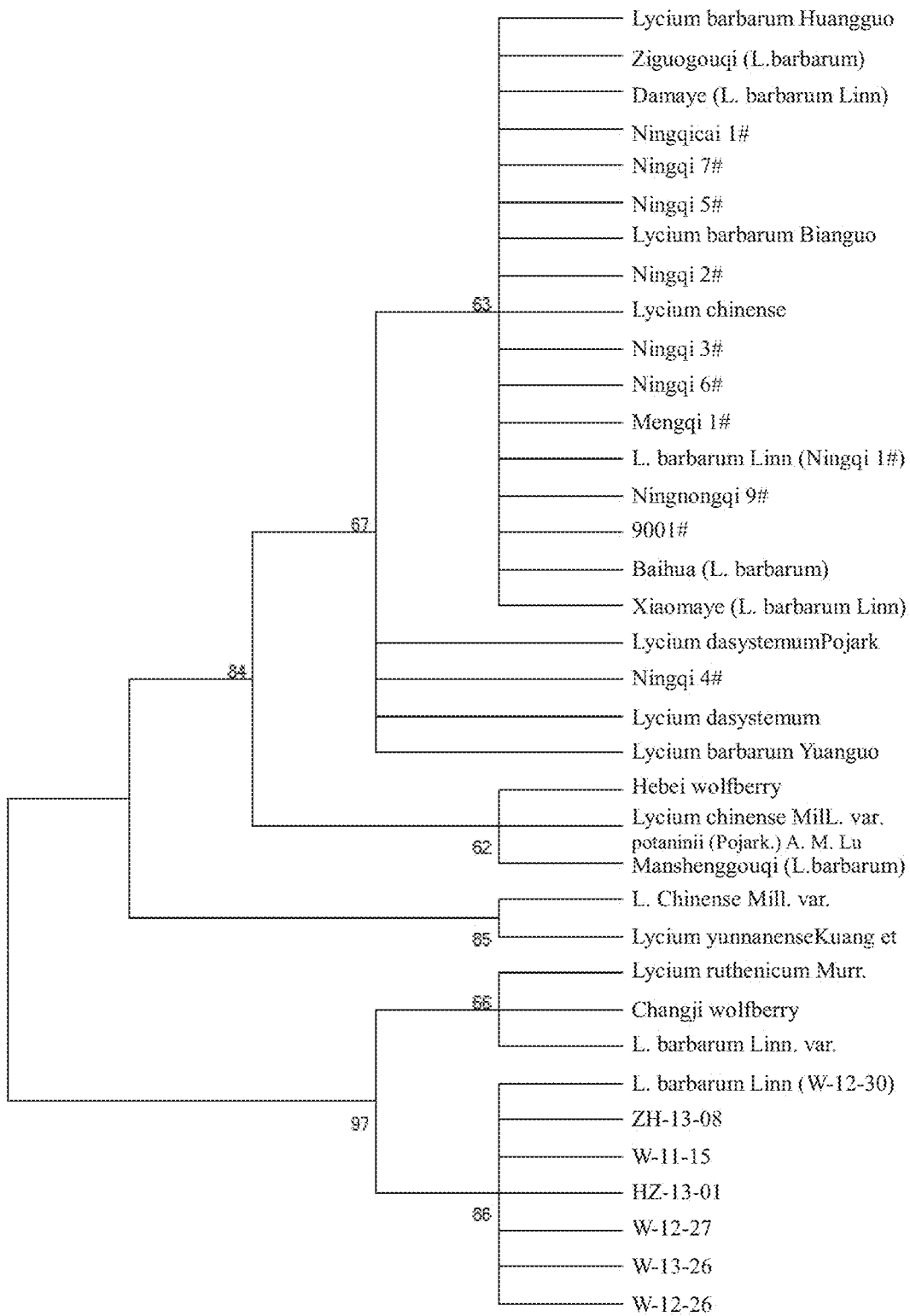
FIG. 4 shows a NJ phylogenetic tree constructed by trnG-trnS barcodes in the trnG-trnS barcode database in Embodiment 1.

A phylogenetic tree is constructed by comparing the distribution of intraspecies and interspecies differences (FIG. 4). The clustergram of trNn-TRNS barcode sequences is divided into two branches, Lycium ruthenicum Murr., Changji wolfberry and L. barbarum Linn. var. auranticar-

*pum* K. F. Ching var. nov., as well as 7 black half-bred wolfberry variants by space mutation form one branch, the bootstrap rate is 97; wherein *Lycium ruthenicum* Murr., Changji wolfberry and *L. barbarum* Linn. var. *auranticarpum* K. F. Ching var. nov. are clustered in one branch, with closest genetic relationship; and *L. chinense* Mill. Var. and *Lycium yunnanense* Kuang et A. M. Lu 26 germplasms form one branch, the bootstrap rate is 85; Hebei wolfberry, *Lycium chinense* MilL. var., Manshenggouqi (*L. barbarum*) are clustered in one branch, and the bootstrap rate is 62; *Lycium dasystemum* Pojark, Ningqi 4, *Lycium dasystemum* and *Lycium barbarum* Yuanguo are clustered in one branch, and the bootstrap rate is 67; the remaining 17 germplasms form a branch, with the closest generic relationship; each branch has an internal bootstrap rate over 60, which ensures more reliable identification results.

The above proves that the DNA barcode provided by the present invention can be applied to building a wolfberry phylogenetic tree to be used for studying intra-species and inter-species phylogeny of wolfberries, and futher proves the DNA barcode provided by the present invention is effective and feasible in identification, classification and phylogenetic study of wolfberry species;

In addition, the embodiment of the present invention constructs a trnG-trnS barcode database based on barcode trnG-trnS sequence, which includes *Lycium ruthenicum* Murr., Huangguo wolfberry, *Lycium barbarum* Yuanguo, *Lycium dasystemum*, also local wolfberry species of Ningxia, the northern, Xinjiang. Yunnan and Hebei, and representative wolfberry species of different sources, such as hybrid population, space mutation population and ploidy population, which are all known as China's representative species, hence, it provides an effective bases for classification and identification of wolfberry species.

Align the trnG-trnS sequence of a sample to be identified with the sequence in the trNg-TRNS barcode database, effectively identify the species of the wolfberry and determine the interspecies relationship of the wolfberry, and further determine the interspecies relationship between the wolfberry to be identified and the wolfberry in the barcoding database, thereby providing an effective basis for classification and identification of wolfberry species.

Example 1 Identification of Species of *Lycium ruthenicum* Murr. Using Barcode Database 1. Sampling Taking ten wolfberry samples numbered SD 18-01, SD 18-02, ZJ 18-03, ZJ 18-04, No. 1 Huang, Dayezihuang, P1806, 16-23-8-10, 16-18-16-15 and *2-184 to align with barcode in trnG-trnS barcode database of a part of wolfberry samples in embodiment 1. As this wolfberry species can not be identified by a morphological method, DNA barcoding is used in this experiment.

TABLE 4

Number and place of origin of wolfberry test samples

| Samples | Place of origin | Samples | Place of origin |
|---|---|---|---|
| SD 18-01 | Shandong | Dayezihuang | Ningxia |
| SD 18-02 | Shandong | P1806 | Ningxia |
| ZJ 18-03 | Zhejiang | 16-23-8-10 | Ningxia |

TABLE 4-continued

Number and place of origin of wolfberry test samples

| Samples | Place of origin | Samples | Place of origin |
|---|---|---|---|
| ZJ 18-04 | Zhejiang | 16-18-16-15 | Ningxia |
| No.1 Huang | Ningxia | *2-184 | Ningxia |

2. DNA Extraction and Concentration Detection, PCR Amplification, PCR Product Cloning, Sequence Sequencing and Analysis are Consistent with that Described in Embodiment 1.

3. Analysis of Sequence Results

Figure 5:
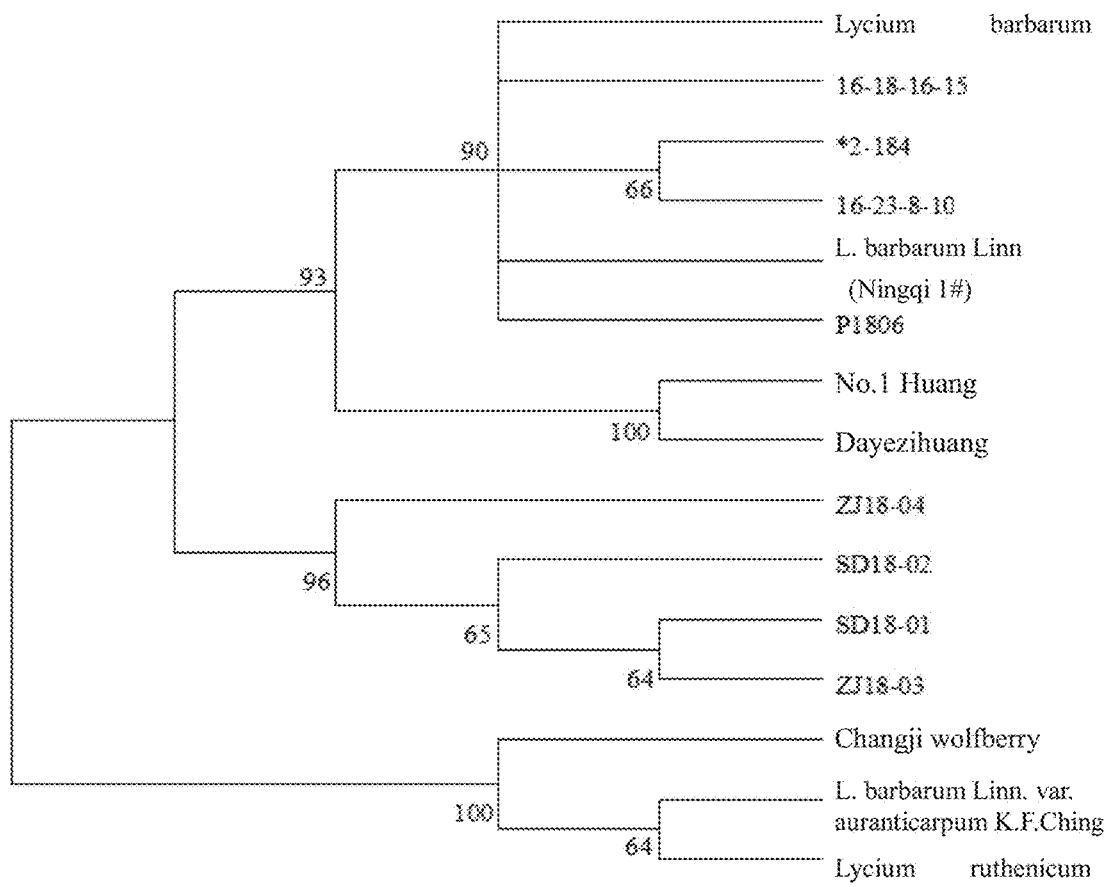
FIG. 5 shows a NJ phylogenetic tree of the wolfberry samples in Example 1 based on trnG-trnS barcode database.

Software MEGA7.0 is applied to conduct sequence alignment and cluster analysis, and NJ (Neighbor-joining) method is used to construct a phylogenetic tree as shown in FIG. 5. The clustergram of trnG-trnS barcode sequences is divided into two branches, *Lycium barbarum* Hongguo and *Lycium ruthenicum* Murr. are clearly identified. *L. barbarum* Linn. var. *auranticarpum* K. F. Ching var. nov., *Lycium ruthenicum* Murr. and Changji wolfberry is clustered into one branch, with the closest generic relationship; and the bootstrap rate with the other 12 wolfberries is 100, the confidence level is high.

The test samples P1806, 16-23-8-10, 16-18-16-15 and *2-184, and *L. barbarum* Linn (Ningqi 1) (number 1 in the barcode database), as well as *Lycium barbarum* Huangguo (number 24 in the barcode database) are clustered into one branch, with the closest generic relationship and the bootstrap rate is 90; wherein *2-184 and 16-23-8-10 are clustered into one sub-branch, they have the closest generic relationship and the bootstrap rate is 66. The above 4 test samples (1806, 16-23-8-10, 16-18-16-15 and *2-184) are obtained by hybridization of different varieties of *Lycium barbarum* L. (Ningxia wolfberry) or hybridization of the hybridized offsprings. From both Genetic distance and cluster analysis, it can be concluded that the 4 test samples have the closest generic relationship with *Lycium barbarum* L. (Ningxia wolfberry).

The 4 test samples No. 1 Huang and Dayezihuang are in one branch, which are the closest generic relationship, and the bootstrap rate is 100, so the confidence level is high. SD 18-01, SD 18-02, ZJ 18-03 and ZJ 18-04 are clustered in one branch, they have the closest generic relationship, with the bootstrap rate of 96, and the confidence level is high. No. 1 Huang is the stage of *L. barbarum* Linn(Ningqi 1) when it is under bud mutation and the fruits are in yellow color; SD 18-01, SD 18-02, ZJ 18-03 and ZJ 18-04 are Chinese wolfberries in Shandong and Zhejiang regions, so the branch of the test sample No. 1 Huang is close to the branch of *Lycium barbarum* L. (Ningxia wolfberry), having the closest generic relationship; while it has a poor relationship with the branch of SD 18-01, SD 18-02, ZJ 18-03 and ZJ 18-04; the bootstrap rate of each branch is higher than 60, and the confidence level is high. This indicates that trnG-trnS barcode sequence and the barcode database constructed by the method of the invention are helpful in classification and species identification for wolfberry samples from different regions.

The genetic distance is calculated by using the K2P model (Kimura 2-parameter Model) and software MEGA7.0, as shown in Table 5. The genetic distance between *L. barbarum* Linn. var. *auranticarpum* K. F. Ching var. nov., *Lycium ruthenicum* Muff., *L. barbarum* Linn(Ningqi 1) and P1806 is 0.00000, it's a minimum. And the genetic distance between No. 1 Huang and ZJ18-04 is 0.009192, it's a maximum.

TABLE 5

Analysis on identification of genetic distance of wolfberries by trnG-trnS

| | L. barbarum Linn(Ningqi 1) | L. barbarum Linn. var. auranticarpum K. F. Ching var. nov. | Lycium ruthenicum Murr. | Lycium barbarum Huangguo | Changji wolfberry |
|---|---|---|---|---|---|
| L. barbarum Linn1 (Ningqi 1) | | | | | |
| L. barbarum Linn. var. auranticarpum K. F. Ching var. nov. | 0.006108 | | | | |
| Lycium ruthenicum Murr. | 0.006108 | 0.000000 | | | |
| Lycium barbarum Huangguo | 0.001217 | 0.007335 | 0.007335 | | |
| Changji wolfberry | 0.006116 | 0.000609 | 0.000609 | 0.007344 | |
| SD18-01 | 0.006733 | 0.007340 | 0.007344 | 0.007965 | 0.007965 |
| SD18-02 | 0.005498 | 0.006104 | 0.006108 | 0.006726 | 0.006730 |
| 16-18-16-15 | 0.000608 | 0.006721 | 0.006721 | 0.001827 | 0.006729 |
| No.1 Huang | 0.005497 | 0.008565 | 0.008565 | 0.006726 | 0.009186 |
| Dayezihuang | 0.003659 | 0.006722 | 0.006722 | 0.004884 | 0.007341 |
| *2-184 | 0.000608 | 0.006721 | 0.006721 | 0.001827 | 0.006729 |
| P1806 | 0.000000 | 0.006108 | 0.006108 | 0.001217 | 0.006116 |
| 16-23-8-10 | 0.001217 | 0.007335 | 0.007335 | 0.002438 | 0.007344 |
| ZJ18-03 | 0.006115 | 0.006721 | 0.006725 | 0.007345 | 0.007344 |
| ZJ18-04 | 0.006119 | 0.007344 | 0.007344 | 0.007350 | 0.007959 |

| | SD18-01 | SD18-02 | 16-18-16-15 | No.1 Huang | Dayezihuang |
|---|---|---|---|---|---|
| SD18-02 | 0.001216 | | | | |
| 16-18-16-15 | 0.007349 | 0.006111 | | | |
| No.1 Huang | 0.009192 | 0.007955 | 0.006111 | | |
| Dayezihuang | 0.007344 | 0.006112 | 0.004271 | 0.001827 | |
| *2-184 | 0.007349 | 0.006111 | 0.001217 | 0.006111 | 0.004271 |
| P1806 | 0.006733 | 0.005498 | 0.000608 | 0.005497 | 0.003659 |
| 16-23-8-10 | 0.007965 | 0.006726 | 0.001827 | 0.006726 | 0.004884 |
| ZJ18-03 | 0.001827 | 0.000608 | 0.006730 | 0.008570 | 0.006725 |
| ZJ18-04 | 0.002442 | 0.001220 | 0.006734 | 0.009192 | 0.007344 |

| | *2-184 | P1806 | 16-23-8-10 | ZJ18-03 | ZJ18-04 |
|---|---|---|---|---|---|
| P1806 | 0.000608 | | | | |
| 16-23-8-10 | 0.000608 | 0.001217 | | | |
| ZJ18-03 | 0.006730 | 0.006115 | 0.007345 | | |
| ZJ18-04 | 0.006734 | 0.006119 | 0.007350 | 0.001830 | |

Example 2 the Identification of Species of *Lycium ruthenicum* Murr. Using Barcode Database 1. Sampling 8 wolfberry samples numbered B1, B3, B5, B8, B9-1, HB, H5 and 15-1 are taken. They cannot be identied by morphological method. The method of the present invention based on DNA barcode database is used to perform species identification. DNA barcode alignments of the 8 samples with barcode in trnG-trnS barcode database in embodiment 1.

TABLE 6

Number and place of origin of wolfberry test samples

| Sample | Place of origin | Sample | Place of origin |
|---|---|---|---|
| B1 | Qinghai | B9-1 | Qinghai |
| B3 | Qinghai | HB | Ningxia |
| B5 | Qinghai | H5 | Ningxia |
| B8 | Qinghai | 15-1 | Ningxia |

2. DNA Extraction and Concentration Detection, PCR Amplification, PCR Product Cloning, Sequence Sequencing and Analysis are Consistent with that Described in Embodiment 1.

3. Analysis of Sequence Results

Figure 6:
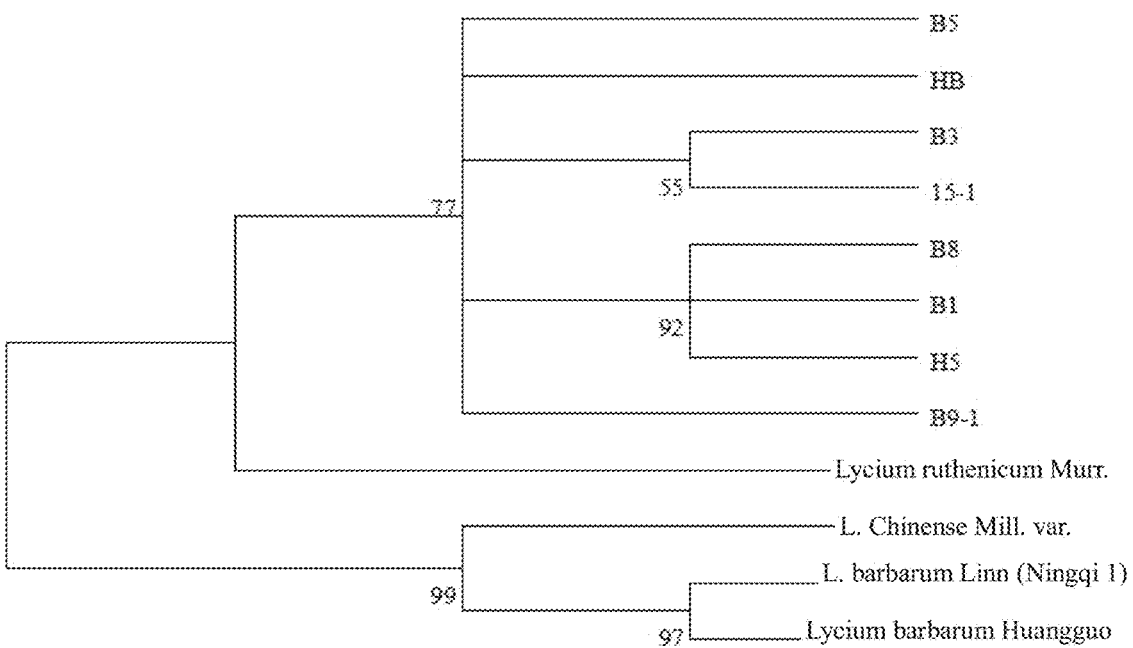
FIG. 6 shows a NJ phylogenetic tree of the wolfberry samples in Example 2 based on trnG-trnS barcode database.

MEGA7.0 software is applied to conduct sequence alignment and cluster analysis, and NJ method is used to construct a phylogenetic tree as shown in FIG. 6. The clustergram of trnG-trnS barcode sequences is divided into two branches. *Lycium barbarum* Hongguo and *Lycium rutheni-*

*cum* Murr. are clearly detected. *L. barbarum* Linn (Ningqi 1), *Lycium barbarum* Huangguo and *L. chinense* Mill. var are clustered into one branch, with the closest generic relationship. They all belong to *Lycium barbarum* Hongguo. The bootstrap rate with the other 9 wolfberries is 99, so the confidence level is high.

8 *Lycium ruthenicum* Murr. test samples and *Lycium ruthenicum* Murr. (number 12 in the barcode database) are clustered into one branch, with the bootstrap rate of 77, and the confidence level is high. Wherein the test sample B3 and 15-1 can clustered into one sub-branch, the both have the closest generic relationship, with the bootstrap rate of 55. Sample B8, B1 and H5 are clustered into one branch, they have the closest generic relationship, with the bootstrap rate of 92, and the confidence level is high. This indicates that trnG-trnS barcode sequence and the barcode database constructed by the method of the invention are helpful in classification and identification of *Lycium ruthenicum* Murr. samples from different regions that cannot be identified by morphological method.

The genetic distance is calculated by using the K2P model (Kimura 2-parameter Model) and software MEGA7.0, as shown in Table 7. The genetic distance between B9-1 and *Lycium ruthenicum* Murr. is 0.000608, it's a minimum. They have the closest generic relationship. The genetic distance between B8 and *Lycium barbarum* Huangguo is 0.011048, it's a maximum. It's a distant genetic relationship between them.

TABLE 7

Analysis on identification of genetic distance of *Lycium ruthenicum* Murr. by trnG-trnS

|  | *L. barbarum* Linn (Ningqi 1#) | *Lycium ruthenicum* Murr. | *Lycium barbarum* Huangguo | *L. Chinense* Mill. var. | B5 | B1 |
|---|---|---|---|---|---|---|
| *L. barbarum* Linn (Ningqi 1) |  |  |  |  |  |  |
| *Lycium ruthenicum* Murr. | 0.004885 |  |  |  |  |  |
| *L. barbarum* Huangguo | 0.001217 | 0.006111 |  |  |  |  |
| *L. Chinense* Mill. var. | 0.001836 | 0.003063 | 0.003063 |  |  |  |
| B5 | 0.009205 | 0.004279 | 0.010444 | 0.007378 |  |  |
| B1 | 0,006733 | 0.001829 | 0.007964 | 0.004909 | 0.005511 |  |
| B8 | 0.00981 | 0.004888 | 0.011048 | 0.007991 | 0.008592 | 0.004281 |
| HB | 0.006111 | 0.001217 | 0.007341 | 0.004291 | 0.004279 | 0.003052 |
| H5 | 0,008581 | 0.003664 | 0.009816 | 0.006759 | 0.00736 | 0.003054 |
| B9-1 | 0.005498 | 0.000608 | 0.006726 | 0.003676 | 0.004893 | 0.00244 |
| B3 | 0.006115 | 0.001218 | 0.007344 | 0.004291 | 0.00428 | 0.003051 |
| 15-1 | 0,00673 | 0.001828 | 0.007961 | 0.004906 | 0.004893 | 0.003664 |

|  | B8 | HB | H5 | B9-1 | B3 | 15-1 |
|---|---|---|---|---|---|---|
| HB | 0.006117 |  |  |  |  |  |
| H5 | 0.006128 | 0.004891 |  |  |  |  |
| B9-1 | 0,005502 | 0.001826 | 0.004277 |  |  |  |
| B3 | 0.006115 | 0.002439 | 0.00489 | 0.001828 |  |  |
| 15-1 | 0.006733 | 0.003049 | 0.005506 | 0.002438 | 0.001828 |  |

The invention claimed is:

1. A method comprising the following the steps:
constructing a barcode database of *Lycium chinensis* comprising 36 trnG-trnS barcodes corresponding to 36 *Lycium chinensis* varieties, wherein the barcode database comprises the 36 barcodes comprising SEQ ID NO: 1-36;
obtaining a trnG-trnS sequence from a *Lycium chinensis* sample to be identified by
(a) extracting genomic DNA from a *Lycium chinensis* sample to be identified;
(b) amplifying fragments of a trnG-trnS barcode from the genomic DNA using primers comprising the nucleotide sequences SEQ ID NO:37 and SEQ ID NO:38 to obtain a PCR product; and
comparing the sequence of the amplified barcode fragment of the sample to be identified to the 36 trnG-trnS sequences in the barcode database.

2. The method of claim 1, wherein the genomic DNA from the sample is extracted using a kit.

3. The method of claim 1, wherein the amplifying is by PCR and the PCR amplification reaction includes pre-denaturation at 94° C. for 2 minutes, then 35 cycles of denaturing at 94° C. for 30 seconds, annealing at 55 C-60° C. for 30 seconds, and extension at 72° C. for 2 minutes, and then incubation at 72° C. for 10 minutes and storage at 4° C.

* * * * *